United States Patent [19]

Dubler et al.

[11] Patent Number: 5,407,834
[45] Date of Patent: Apr. 18, 1995

[54] PHENCYCLIDINE AND PHENCYCLIDINE METABOLITES ASSAY, TRACERS, IMMUNOGENS, ANTIBODIES AND REAGENT KIT

[75] Inventors: Robert E. Dubler, Gurnee, Ill.; Mary P. Frintner, Elk Grove, Ill.; Jonathan Grote, Grayslake, Ill.; Gregg A. Hadley, St. Louis, Mo.; David J. Hawksworth, Vernon Hills, Ill.; Hal D. Hopkins, Chicago, Ill.; Daniel S. Nam, Lake Elsinore, Calif.; Frank S. Ungemach, Lake Villa, Ill.; Larry K. Wray, Highland Park, Ill.

[73] Assignee: Abbott Laboratories, Abbott Park, Ill.

[21] Appl. No.: 831,762

[22] Filed: Apr. 27, 1992

Related U.S. Application Data

[60] Division of Ser. No. 529,988, May 29, 1990, Pat. No. 5,155,212, which is a continuation-in-part of Ser. No. 866,193, May 21, 1986, abandoned.

[51] Int. Cl.⁶ .................. G01N 33/542; G01N 33/577; C12N 5/20; C07K 15/28
[52] U.S. Cl. .................... 436/537; 436/536; 436/548; 436/816; 435/240.27; 530/388.9; 530/389.8; 424/141.1
[58] Field of Search .......... 530/386.9, 389.8; 544/243, 333, 375; 546/15, 21, 22, 196; 435/240.27; 549/223; 436/536, 537, 546, 808, 816, 548; 424/141.1

[56] References Cited

U.S. PATENT DOCUMENTS

| | | | |
|---|---|---|---|
| 4,196,185 | 4/1980 | Focella et al. | 424/1.1 |
| 4,255,329 | 3/1981 | Ullman | 540/589 |
| 4,281,065 | 7/1981 | Lin et al. | 435/188 |
| 4,351,760 | 9/1982 | Khanna et al. | 530/408 |
| 4,420,568 | 12/1983 | Wang et al. | 436/536 |
| 4,446,065 | 5/1984 | Lin et al. | 435/188 |
| 4,476,228 | 10/1984 | Huckzermeir et al. | 436/500 |
| 4,476,229 | 10/1984 | Fino et al. | 436/500 |
| 4,481,136 | 11/1984 | Khanna et al. | 435/188 |
| 4,492,762 | 1/1985 | Wang et al. | 436/537 |
| 4,510,251 | 4/1985 | Kirkemo et al. | 436/536 |
| 4,585,862 | 4/1986 | Wang et al. | 544/319 |
| 4,588,697 | 5/1986 | Khanna et al. | 436/518 |
| 4,593,089 | 6/1986 | Wang et al. | 536/13.6 |
| 4,681,859 | 7/1987 | Kramer | 436/501 |
| 4,939,264 | 7/1990 | Heiman et al. | 436/537 |
| 5,124,457 | 6/1992 | Ungenach et al. | 546/196 |
| 5,221,629 | 6/1993 | Ungemach et al. | 436/536 |

FOREIGN PATENT DOCUMENTS

| | | |
|---|---|---|
| 0386644 | 9/1990 | European Pat. Off. |
| 2111476 | 7/1983 | United Kingdom ........ C07D 34/86 |

OTHER PUBLICATIONS

S. Seaver (Aug., 1994) Genetic Engineering News, pp. 10 and 21.
Kaul et al (1980) Clinical Toxicology 16(1):7–15.
Owens et al (1986) Drug Metabolism and Disposition 14(1):52–58.

(List continued on next page.)

*Primary Examiner*—Kay K. A. Kim
*Attorney, Agent, or Firm*—Lawrence S. Pope

[57] ABSTRACT

The present invention is directed to a fluorescence polarization assay for phencyclidine and phencyclidine derivatives, to the various components needed for preparing and carrying out such an assay, and to methods of making these components. Specifically, tracers, immunogens and antibodies are disclosed, as well as methods for making them, and a reagent kit containing them. The tracers and the immunogens are made from substituted phencyclidine compounds. A fluorescein moiety is included in the tracer, while a poly(amino acid) forms a part of the immunogen. The assay is conducted by measuring the degree of polarization retention of plane polarized light that has been passed through a sample containing antiserum and tracer.

12 Claims, 5 Drawing Sheets

OTHER PUBLICATIONS

Shipchandler, M. T., "4'-[Aminomethyl]fluorescein and its N-Alkyl Derivatives: Useful Reagents in Immunodiagnostic Techniques", Analytical Biochemistry, 162:89-101(1987).

Miceli, Joseph N., et al., "An Improved Method for the Quantitation of Phencyclide (PCP) in Biological Samples Utilizing Nitrogen-Detection Gas Chromatography", Journal of Analytical Toxicology, 5:29-32, Jan.-/Feb., 1981.

Lewellen, Larry J., et al., "Nitrogen-Sensitive Gas Chromatographic Detection and Quantitation of Nanogram Levels of Phencyclidine in Whole Blood", Journal of Analytical Toxicology, 72-75, Mar./Apr. 1979.

Egen, N. B., et al., "Isolation of Monoclonal Antibodies to Phencyclidine from Ascites Fluid by Preparative Isoelectric Focusing in the RotoFor," Anal. Biochemistry 172, 488-494 (1988).

Tillotson, J. A., et al., "The Fluorometric Apoprotein Titration of Urinary Riboflavin," Anal. Biochemistry 107, 214-219 (1980).

Rhodes, M. B., et al., "The Flavoprotein-Apoprotein System of Egg White," J. Biol. Chemistry 234, No. 8, 2060 (1959).

Nishikimi et al., "Flavin-Protein Interaction in Egg White Flavoprotein," J. Biochem. 73, 1233-1242 (1973).

Murthy, U.S., et al., "The Interaction of Riboflavin with a Protein Isolated from Hen's Egg White: A Spectrofluorimetric Study," Biochemica et Biophysica Acta, 434, 69-81 (1976).

Heveran, J. E., "Determination of Phencyclidine by Radioimmunoassay, " J. Forensic Sciences, vol. 25, No. 1, pp. 79-87 (1980).

EXAMPLE XIII

EXAMPLE XIV

EXAMPLE XVI

EXAMPLE XV

EXAMPLE X

EXAMPLE VI

EXAMPLE IX

EXAMPLE XII

PHENCYCLIDINE AND PHENCYCLIDINE METABOLITES ASSAY, TRACERS, IMMUNOGENS, ANTIBODIES AND REAGENT KIT

CROSS-REFERENCE TO RELATED APPLICATIONS

This application is a divisional application of U.S. Ser. No. 529,988, filed 29 May, 1990, now U.S. Pat. No. 5,155,212, which is a continuation-in-part of U.S. Ser. No. 866,193, filed 21 May, 1986, now abandoned.

BACKGROUND OF THE INVENTION

1. Technical Field

The present invention relates to a method and reagents for performing a fluorescence polarization immunoassay (FPIA) to determine the presence or amount of phencyclidine and phencyclidine metabolites in samples, especially fluid biological samples such as urine, serum or plasma, to a method of making the reagents, and to an assay kit containing the reagents. The invention relates particularly to (1) reagents (tracers and antibodies, and an assay kit containing the tracers and antibodies) for determining the presence or amount of phencyclidine and phencyclidine metabolites in a sampler; (2) immunogen compounds used to raise monoclonal or polyclonal antibodies; (3) synthetic methods for making the tracer and immunogen compounds; and (4) analytical methods for conducting the assay.

2. Background Art

Phencyclidine is a synthetic drug with potent analgesic and anesthetic properties. This drug has been shown to produce serious and prolonged post-anesthetic confusion and delirium. Its tendency to produce hallucinations, euphoria, distortions in perceptions, and feelings of dissociation have lead to illicit use and abuse. Recurring abuse has intensified efforts to prevent its manufacture and distribution. Consistent with these efforts, there exists a need for detection methods which are rapid, reliable and selective for phencyclidine and phencyclidine metabolites.

Phencyclidine is metabolized into two major metabolites, 4-phenyl-4-piperidinocyclohexanol and 1-(1-phenylcyclohexyl)-4-hydroxypiperidine, each of which is excreted mostly in the urine along with the corresponding glucuronide conjugates. Detection of either phencyclidine or phencyclidine metabolites indicates phencyclidine use.

The biological fluid most frequently tested is urine. Urine samples are non-invasive of the body, and are generally more accessible than blood samples. However, testing of other biological materials is also possible.

In the past, urine samples have been tested for the presence of phencyclidine and phencyclidine metabolites by thin layer chromatography (TLC), gas chromatography (GC) or high performance liquid chromatography (HPLC) assays. A significant disadvantage of each of these methods is that the assay time involved in these methods is typically lengthy.

In assays for phencyclidine, phencyclidine metabolites, and other substances, competitive binding immunoassays have provided a more satisfactory alternative. Typically, competitive binding immunoassays are used for measuring ligands in a test sample. (For purposes of this disclosure, a "ligand" is a substance of biological interest to be quantitatively determined by a competitive binding immunoassay technique). The ligands compete with a labeled reagent (a "ligand analog" or "tracer") for a limited number of ligand binding sites on antibodies specific to the ligand and ligand analog. The concentration of ligand in the sample determines the amount of ligand analog which binds to the antibody, and the amount of ligand analog that will bind to the antibody is inversely proportional to the concentration of ligand in the sample, because the ligand and the ligand analog each bind to the antibody in proportion to their respective concentrations.

FPIA techniques provide a quantitative means for measuring the amount of tracer-antibody conjugate produced in a competitive binding immunoassay. Such procedures are based on the principle that a fluorescent labeled compound, when excited by plane polarized light, will emit fluorescence having a degree of polarization inversely related to its rate of rotation. Accordingly, when a tracer-antibody conjugate having a fluorescent label is excited with plane polarized light, the emitted light remains highly polarized because the fluorophore is constrained from rotating between the time that light is absorbed and emitted. In contrast, when an unbound tracer is excited by plane polarized light, its rotation is much faster than the corresponding tracer-antibody conjugate and the molecules become more randomly oriented. As a result, the light emitted from the unbound tracer molecules is depolarized.

A problem that heretofore has prevented the accurate determination of phencyclidine and other "drugs of abuse" in urine by FPIA techniques is that of riboflavin interference. Riboflavin, or vitamin $B_2$, is a common constituent of many foods and of commercially available vitamin supplements. Riboflavin is excreted primarily in the urine and has a fluorescence spectrum quite similar to that of fluorescein. As a result, the presence of riboflavin in even moderate amounts in urine samples creates an interference which can produce erroneous data. While ordinary consumption of riboflavin is unlikely to produce more than trace amounts of riboflavin in the urine, test results can readily be distorted by the consumption of excessive quantities of vitamin supplements by persons wishing to prevent detection of phencyclidine.

The present invention offers an advance in the art in that tracers, a method for making the tracers, and an assay using the tracers and monoclonal or polyclonal antibodies are provided specifically for the determination of phencyclidines and phencyclidine metabolites without riboflavin interference.

SUMMARY OF THE INVENTION

The present invention is directed to a fluorescence polarization immunoassay for phencyclidine and phencyclidine metabolites; to tracers, immunogens and antibodies; to a reagent kit containing tracers and antibodies for use in the assay; and to methods for making the tracers, immunogens and antibodies.

A first aspect of the invention relates to the discovery of unique tracers and immunogens having novel structures. According to the first aspect of the invention, the tracers and the immunogens can both be represented by each of the structural formulas shown in FIGS. 5 and 20 wherein:

W is CH or N;

R is a linking group including up to 4 heteroatoms, and having a total of from 0 to 8 carbon atoms and heteroatoms, arranged in a straight or branched chain, and containing up to one aliphatic or aromatic ring structure, said heteroatoms being O, N, S, P or F;

Z is NH, CO, CNH, or OCO;

n is 0 or 1 when W is N and n is 1 when W is CH; and

Q is a poly(amino acid), a poly(amino acid) derivative, fluorescein or a fluorescein derivative.

When Q is a poly(amino acid) or a derivative thereof, the compound can be used as an immunogen. When Q is fluorescein or a derivative thereof, the compound can be used as a tracer.

A second aspect of the invention relates to monoclonal or polyclonal, preferably monoclonal, antibodies raised against the novel immunogens of the invention. According to the second aspect of the invention, monoclonal or polyclonal antibodies are prepared in response to a compound according to one of the aforementioned structural formulas (FIGS. 5 or 20), when Q is a poly(amino acid) or a derivative thereof.

According to a third aspect of the invention, an immunogen is made by a method comprising the step of coupling a compound represented by either of the structural formulas shown in FIGS. 3 or 21, wherein:

W is CH or N;

R is a linking group including up to 4 heteratoms, and having a total of from 0 to 8 carbon atoms and heteroatoms, arranged in a straight or branched chain, and containing up to one aliphatic or aromatic ring structure, said heteroatoms being O, N, S, P or F;

Z is $NH_2$, COOH, CN, CHO or OH; and n is 0 or 1 when W is N and n is 1 when W is CH; with a poly(amino acid) or a derivative of a poly(amino acid).

According to a fourth aspect of the invention, a method is provided for making a tracer by coupling a compound represented by either of the structural formulas shown in FIGS. 2 or 21, wherein:

W is CH or N;

R is a linking group including up to 4 heteroatoms, and having a total of from 0 to 8 carbon atoms and heteroatoms, arranged in a straight or branched chain, and containing up to one aliphatic or aromatic ring structure, said heteroatoms being O, N, S, P or F;

Z is $NH_2$, COOH, CN, CHO or OH; and n is 0 or 1 when W is N and n is 1 when W is CH; with fluorescein or a derivative of fluorescein.

A fifth aspect of the invention relates to the elimination of potential fluorescence interference by riboflavin. Riboflavin binding protein (RBP) is added either directly to each sample, or to one or more of the reagents utilized in the assay, wherein it binds all riboflavin which may be present in the sample into RBP-riboflavin complexes, thus eliminating fluorescence interference. Other fluorescence-quenching substances may also be utilized for this purpose.

According to a sixth aspect of the invention, a process for detecting or measuring the concentration of phencyclidine and phencyclidine metabolites is provided. A sample is contacted with a phencyclidine derivative antiserum, and with a fluorescein-containing phencyclidine derivative capable of producing a detectable fluorescence polarization response to the presence of the phencyclidine derivative antiserum. Plane polarized light is then passed through the solution to obtain a fluorescence polarization response, and this response is detected as a measure of the amount of phencyclidine and phencyclidine metabolite in the sample.

A seventh aspect of the present invention relates to a stabilized reagent kit which is useful for determining the presence or amount of phencyclidine and phencyclidine metabolites in a sample. The reagent kit contains novel tracers, and salts thereof, which are useful as reagents in the novel method of the present invention. Other components of the reagent kit include: (1) a solution containing an amount of riboflavin binding protein which is effective to reduce fluorescence interference by riboflavin; (2) a monoclonal or polyclonal antibody reagent which has been raised against an immunogen which is capable of specifically recognizing and binding phencyclidine and phencyclidine metabolites and the novel tracer reagents of the present invention; and (3) a wash solution containing a sufficient amount of dimethylformamide and a sufficient amount of butanol to wash the probe of an automated or semiautomated instrument used to conduct the assay, with the result that carryover of phencyclidine from one sample to the next sample is reduced.

Further objects and attendant advantages of the invention will be best understood from a reading of the Detailed Description of the Invention taken together with the Examples and appended drawings.

BRIEF DESCRIPTION OF THE DRAWINGS

In the Figures contained in the drawings, the symbol "Fl" represents fluorescein or a fluorescein derivative and the various other symbols are defined in the Detailed Description of the Invention.

FIG. 10 represents a precursor for the tracers shown in FIGS. 7 and 9.

DETAILED DESCRIPTION OF THE INVENTION

The various aspects of the invention will now be discussed in relation to the Figures and/or the Examples.

The present invention involves the use of fluorescein and derivatives of fluorescein. In particular, a necessary property of fluorescein and its derivatives for the usefulness of the tracer compounds of the present invention is the fluorescence of fluorescein. Fluorescein exists in two tautomeric forms, illustrated in FIG. 4, depending on the acid concentration (pH) of the environment. In the open (acid form), there are a number of conjugated double bonds which make that form of fluorescein (and compounds containing a fluorescein moiety) capable of absorbing blue light and emitting green fluorescence after an excited state lifetime of about 4 nanoseconds. When the open and closed forms coexist, the relative concentration of molecules in the open and closed forms is easily altered by adjustment of the pH level. Generally, the tracer compounds of the present invention exist in solution as biologically acceptable salts such as sodium, potassium, ammonium and the like, which allows the compounds to exist in the open, fluorescent form, when employed in the analytical methods of the present invention. The specific salt present will depend on the buffer employed to adjust the pH level. For example, in the presence of a sodium phosphate buffer, the compounds of the present invention will generally exist in the open form, as a sodium salt.

As used herein, the term "fluorescein," either as an individual compound or as a component of a larger compound, is meant to include both the open and closed forms, if they exist for a particular molecule, except in the context of fluorescence. An open form is necessary for the fluorescence to occur.

Figure 4:
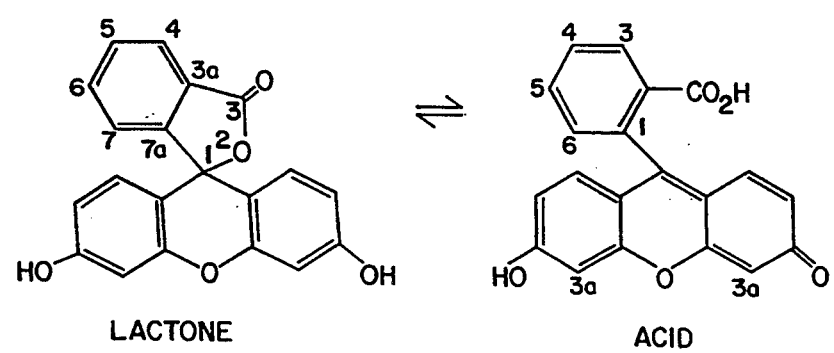
FIG. 4 shows the alternate structural formula and names of the fluorescein moiety included in the tracers of the present invention.

The numbering of carbon atoms of the fluorescein molecule varies, depending upon whether the open or closed form of the molecule is considered. Accordingly, the literature concerning fluorescein and its compounds is not uniform as to carbon atom numbering. In the closed form, the para-carbon to the carbonyl of the lactone on the phenyl ring is numbered 6 (this is sometimes denominated "isomer II"). In the open form, the para-carbon to the carboxylic acid group on the phenyl ring is numbered 5 (this is sometimes denominated "isomer I"). FIG. 4 illustrates these isomers. For the purpose of this disclosure, the numbering of the closed form is adopted because the raw materials used in the syntheses are most popularly numbered with that system. The carbon atom of fluorescein and its compounds which is opposite the carboxyl group is therefore numbered "6" for the purposes of the present disclosure.

A tracer which is not complexed to an antibody is free to rotate in less than the time required for absorption and re-emission of fluorescent light. As a result, the re-emitted light is relatively randomly oriented so that the fluorescence polarization of a tracer not complexed to an antibody is low, approaching zero. Upon complexing with a specific antibody, the tracer-antibody complex thus formed assumes the rotation of the antibody molecule which is slower than that of the relatively smaller tracer molecule, thereby increasing the polarization observed. Therefore, when a ligand competes with the tracer for antibody sites, the observed polarization of fluorescence of the tracer-antibody complex becomes a value somewhere between that of the tracer and tracer-antibody complex. If a sample contains a high concentration of the ligand, the observed polarization value is closer to that of the free tracer, i.e., low. If the test sample contains a low concentration of the ligand, the polarization value is closer to that of the bound tracer, i.e., high. By sequentially exciting the reaction mixture of an immunoassay with vertically and then horizontally polarized light and analyzing only the vertical component of the emitted light, the polarization of fluorescence in the reaction mixture may be accurately determined. The precise relationship between polarization and concentration of the ligand to be determined is established by measuring the polarization values of calibrators with known concentrations. The concentration of the ligand can be extrapolated from a standard curve prepared in this manner.

The particular tracers, immunogens and antibodies formed in accordance with this invention have been found to produce surprisingly good assays, as will be demonstrated later in this disclosure.

The Reagents and Reagent Kit

Figure 5:
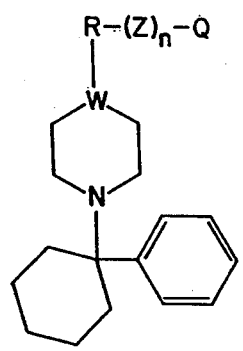
FIG. 5 shows a general structural formula for the tracers and the immunogens of the present invention.
Figure 20:
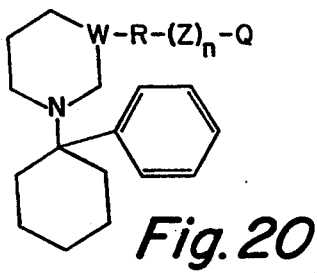
FIG. 20 shows another general structural formula for the tracers and the immunogens of the present invention.

Both the immunogens and the tracers of the present invention are represented by the general structural formulas described in the Summary of the Invention, and illustrated in FIGS. 5 and 20. When Q is a poly(amino acid), the structure represents the immunogen; when Q is a fluorescein derivative, the structure represents the tracer.

An objective of the assay of the present invention is to have competition between phencyclidine and phencyclidine metabolites and the tracer for the recognition sites of the antibody. Great variations in the structure of the haptens and tracers are allowed in achieving this goal. For the purposes of this invention, "haptens" are precursors of the immunogens, comprising generally a substituted phencyclidine derivative and a linking group to the poly(amino acid) carrier.

The Structure of the Immunogens

Usable monoclonal or polyclonal antibodies can be produced from a variety of phencyclidine derivatives. Such antibodies are useful in a phencyclidine and phencyclidine metabolites assay according to the invention when combined with the appropriate tracer.

Figure 6:
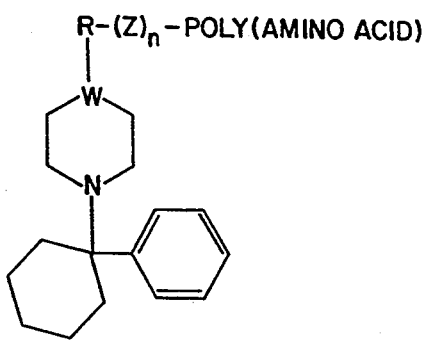
FIG. 6 shows a general structural formula for the immunogens of the present invention.
Figure 7:
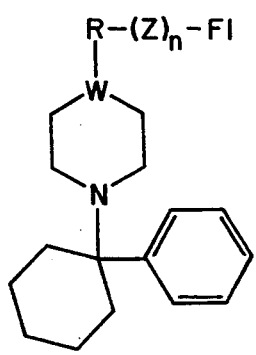
FIG. 7 shows a general structural formula for the tracers of the present invention.
Figure 8:
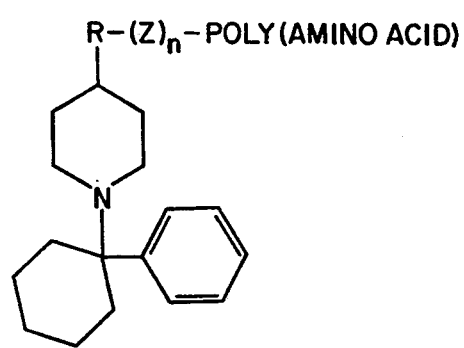
FIG. 8 shows a structural formula for preferred immunogens of the present invention.
Figure 22:
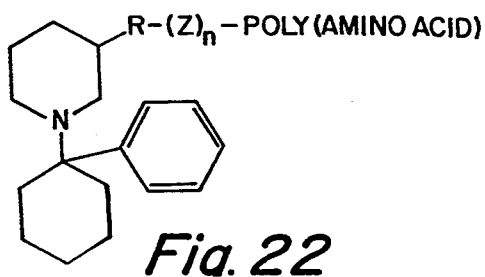
FIG. 22 shows a structural formula for the most preferred immunogens of the present invention.
Figure 23:
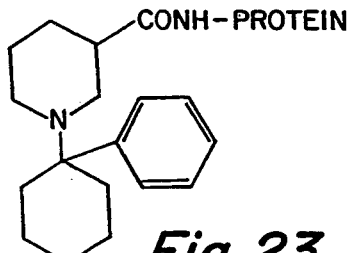
FIG. 23 shows the structure of the most preferred immunogen of the present invention.

The immunogens of the present invention also have the general structural formulas shown in FIGS. 6, 8 and 22. In the preferred form of the invention, the immunogens have the structural formula shown in FIG. 22. The structure of the most preferred immunogen is shown in FIG. 23.

Although thyroglobulin is the poly(amino acid) employed in the most preferred form of the immunogen of the present invention, it should be understood that various protein carriers may be employed, including albumins, serum proteins, e.g., globulins, ocular lens proteins, lipoproteins and the like. Illustrative protein carriers include, in addition to thyroglobulin, bovine serum albumin, keyhole limpet hemocyanin, egg ovalbumin, bovine gamma-globulin, thyroxine binding globulin, etc. Alternatively, synthetic poly(amino acids) may be prepared having a sufficient number of available amino groups, such as lysines, or carboxylic acid groups, such as glutamate. The corresponding glutaraldehyde derivative of the above poly(amino acid) carriers may also be employed when the hapten coupling group is an amino group.

The immunogens can be prepared by coupling a compound of the class shown in FIG. 3 or 21 with a poly(amino acid) or a derivative of a poly(amino acid), as will be discussed in the context of the synthetic method and the Examples below.

The Structure of the Tracers

Figure 9:
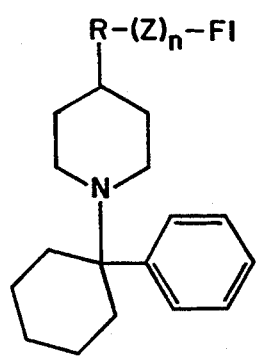
FIG. 9 shows a structural formula for preferred tracers of the present invention.
Figure 10:
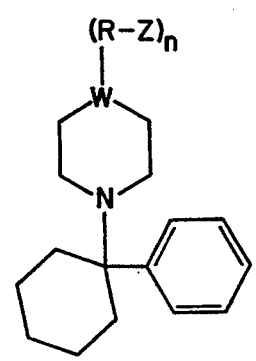
FIG. 10 shows a precursor for the immunogens shown in FIGS. 6 and 8 and for the tracers shown in FIGS. 7 and 9.

The possible variations in the structure of the tracers of the invention are even greater than the possible variations in the structure of the haptens thereof. The tracers of the present invention have the general structural formulas described in the Summary of the Invention and illustrated in FIGS. 5 and 20, where Q represents a fluorescein moiety or a fluorescein derivative. The phencyclidine or phencyclidine derivative can be attached to the fluorescein molecule or fluorescein derivative at any position on the fluorescein molecule or derivative at which the fluorescent properties of the molecule would be retained, including, as numbered in FIG. 4 for the acid form of fluorescein, positions 4, 5 and 3a. In a preferred form of the invention, the tracers have the structural formula shown in FIG. 9. In the most preferred form of the invention, the tracers have the structure shown in FIG. 14.

Figures 1, 11:
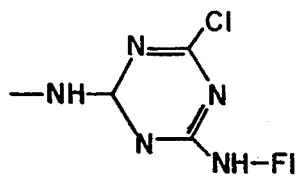
FIG. 11 shows various linkages that couple the fluorescein moiety to the precursor at the Z position in FIG. 10, when
Figures 2, 11:
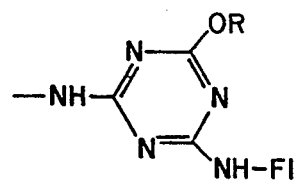
Figures 3, 11:
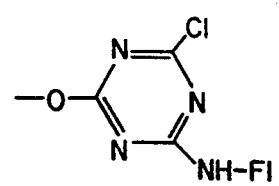
Figures 4, 11:
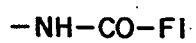
Figures 5, 11:
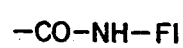
Figures 6, 11:
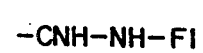
Figures 7, 11:
Figures 8, 11:
Figures 9, 11:
Figures 10, 11:
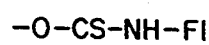

The tracer is a phencyclidine derivative which is linked to a fluorescein derivative by, e.g., an amido, amidino, triazinylamino, carbamido, thiocarbamido, carbamoyl, thiocarbamoyl, or sulfomylcarbamoyl group, as shown in FIG. 11. The tracers are prepared by linking the appropriate fluorescein derivative to a phencyclidine derivative containing an amino, carboxylic acid, hydroxy, imidate, hydrazide, chloroformate, chlorothioformate, chlorosulfonyl-carbamoyl, isocyanate, thioisocyanate, or similar group, as will be discussed in the context of the synthetic method and the Examples below.

By way of example, any of the following fluorescein derivatives can be used:

| | |
|---|---|
| Fl—NH$_2$ | fluorescein amine |
| Fl—CO$_2$H | carboxyfluorescein |
| Fl—NHCOCH$_2$I | a-iodoacetamidofluorescein |
| Fl—NH—(triazine with Cl, N, N, Cl) | 2,4,-dichloro-1,3,5,-triazin-2-yl amino-fluorescein (DTAF) |
| Fl—NH—(triazine with OCH$_3$, N, N, Cl) | 4-chloro-6-methoxy-1,3,5,-triazin-2-ylamino fluorescein |
| Fl—NCS | fluorescein thioisocyanate |

The Antibodies

Although preferred antibodies are raised against immunogens having the structural formula shown in FIG. 22, the most preferred antibodies are raised against immunogens having the structure shown in FIG. 23.

Both polyclonal and monoclonal antibodies recognize specific epitopes on an immunogen. Because polyclonal antibodies consist of a mixture of multiple antibodies, each recognizing a specific epitope, whereas monoclonal antibodies are produced by cells secreting a single antibody recognizing a specific epitope, and because monoclonal antibodies can be produced both in vitro and in vivo, monoclonal antibodies are the preferred antibodies for use in the method of the present invention, and for use in the reagent kit of the invention.

In comparison with an assay of the present invention which employs polyclonal antibodies, an assay of the invention which employs monoclonal antibodies is more desirous in that it: (1) results in a more selective assay; (2) results in an assay having a reduced interference with other compounds which may be present in the sample, and which may cross react with the antibodies and, thus, result in a number of falsely-positive readings for the presence of phencyclidine or phencyclidine metabolites when none was actually present in the sample; (3) eliminates the need for continued animal reimmunization and the labor-intensive process which is associated with such animal reimmunizations; and (4) eliminates the potential for irreproducibility of identical antiserum (because cross-reactive profiles of antibody-producing animals may change, requiring assay reconfiguration, because even carefully maintained animals can die, and because immunization of new animals may not result in the same cross reactivity profile as that originally produced).

Generally, monoclonal antibodies of the present invention may be prepared by injecting animals, such as mice or rats, intraperitoneally, subcutaneously, interveineously, or in some other manner, with an antigen (an immunogen, such as an immunogen having the structure shown in FIG. 23) in order to elicit an immune response in the animals (the production of antibodies which are specific for the antigen). Sera from the animals is then drawn, and the sera is tested to determine the titer of antibody in the sera (to determine whether or not the animal illicited the desired immune response, and to what extent). Those animals in which the desired immune response has been produced are permitted to rest for approximately two to three months. After this two-month to three-month period of time, and approximately three days prior to the anticipated fusion of B-lymphocyte cells (cells which, upon stimulation by antigen, mature into plasma cells which synthesize antibody, and which are also referred to as B cells) with myeloma cells (tumor cells), a boost injection of the antigen is administered to these animals. B-lymphocyte cells are then removed from the spleens of these animals by standard procedures, and the B-lymphocyte cells are then fused with myeloma fusion partners according to standard procedures, such as those described in Kohler and Milsrein, "Continuous Culture of Fused Cells Secreting Antibody of Predefined Specificity," Nature, 256, 495 (1975). The B-lymphocyte-myeloma fusions are then plated in multiwell tissue culture plates containing HAT media, or other suitable media. The resulting cultures are fed with HT media, or other suitable media, and fetal bovine serum or calf bovine serum on or about the fifth and seventh days after the fusion of the cells and then tested on or about the tenth day after the fusion for the presence of antibody which is specific for the antigen. Specific desirable hybrids are then cloned by limiting dilution. (Hybrid cells are diluted in differing amounts of HT media, or other suitable media, and plated out in tissue culture plates in order to isolate a single desired clone.) Established clones are then retested for specificity to a broader panel of cross reactants.

The amount of the resulting monoclonal antibodies produced by a desired clone can then be scaled up to produce a sufficient quantity of antibody for purification in either: (1) tissue culture (by expanding the number of cells in tissue culture, or HT media); or (2) mice for ascites. The monoclonal antibodies can be scaled up in mice by injecting hybrid cells into the abdominal cavity of mice and allowing the cells to grow (usually for about 7 days). The ascites is harvested from the mice by sacrificing the mice, collecting the ascites fluid, and purifying the ascites fluid, as described in Example XVIII. BALB/c mice are the most common strain of laboratory mouse used for this process, and they can be obtained from any mouse vendor, such as Jackson Laboratories, Bar Harbor, Me., or Charles River, Willmington, Mass. Pristane, which may be obtained from Aldrich Chemical Co., Inc., Milwaukee, Wis., should be injected into the mice in order to stimulate their immune systems to produce B and T cells (about two or three weeks before the hybrid cells are injected into the mice), which serve as a feeder layer for the clone cells that are injected into the mice. This is perfomed in order to provide a suitable environment in which the hybrid cells can grow.

Polyclonal antibodies of the present invention are prepared by developing a response in animals to the immunogens described above. The immunogen is administered to animals such as rabbits or sheep by a series of injections, in a manner well-known to those skilled in the art.

Reagent Kit

The novel reagent kit of the present invention for determining the presence or amount of phencyclidine and phencyclidine derivatives in a sample comprises a salt of a first tracer of the formula shown in either FIG. 5 or 20 wherein W, R, Z, n and Q are as defined in the Summary of Invention and monoclonal or polyclonal, preferably monoclonal, antibodies which have been raised against an immunogen having the structure shown in either FIG. 5 or 20 wherein W, R, Z, n and Q are also as defined in the Summary of Invention. Preferably, the reagent kit will also contain an amount of riboflavin binding protein which is effective to reduce fluorescence interference by riboflavin and a wash solution containing dimethylformamide and butanol to wash the probe of an automated or semiautomated instrument used to conduct the assay. While the most preferred tracer for use in the reagent kit is a tracer having the structure shown in FIG. 14, the most preferred antibodies for use in the kit are monoclonal antibodies generated against an immunogen having the structure shown in FIG. 23. The most preferred combination of tracer and antisera for use in the kit are the combination of a tracer having the structure shown in FIG. 14 with monoclonal antibodies generated against an immunogen having the structure shown in FIG. 23.

Synthetic Methods

Figure 1:
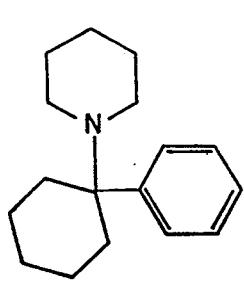
FIG. 1 shows the structure of phencyclidine.
Figure 2:
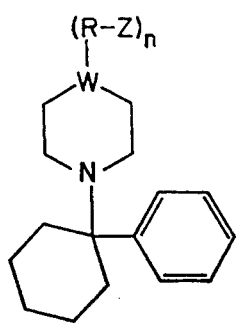
FIG. 2 shows a class of reactants for a method of making a tracer in accordance with the present invention.
Figure 3:
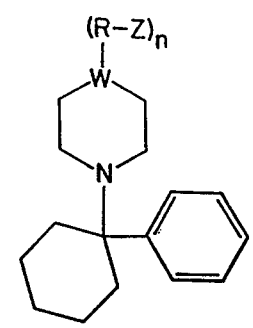
FIG. 3 shows a class of reactants for a method of making an immunogen in accordance with the present invention.
Figure 21:
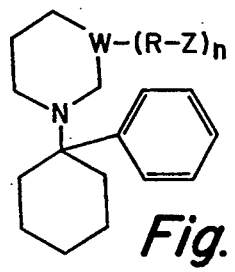
FIG. 21 shows a precursor for the immunogens and tracers of the present invention.

Both the immunogens and the tracers of the present invention can be made from a precursor having the general structural formula shown in FIGS. 2, 3, or 21 wherein:

W is CH or N;

R is a linking group including up to 4 heteroatoms, and having a total of from 0 to 8 carbon atoms and heteroatoms, arranged in a straight or branched chain, and containing up to one aliphatic or aromatic ring structure, said heteroatoms being O, N, S, P or F;

Z is $NH_2$, COOH, CN, CHO, or OH when the preparation is directed to an immunogen, and Z is $NH_2$, COOH, CN, CHO, or OH, when the preparation is directed to a tracer; and n is 0 or 1 when W is N and n is 1 when W is CH.

The Synthesis of the Imunogens

The immunogens of the present invention are made by coupling a hapten, such as those having the general structure shown in FIGS. 2, 3 or 21 when Z is $NH_2$, COOH, CN, CHO or OH, to a poly(amino acid). The poly(amino acid) moiety can be linked to the hapten by an amide, an amidine, an alkyl, a urea, a thiourea, a carbamate, or a thiocarbamate linkage. The hapten is preferably coupled under conditions normally used to form carbamate linkages, which conditions are well known to those skilled in the art. It is most preferred that pH conditions approximating pH 8.0 be used for forming the desired carbamate linkages, as these are the most effective for forming these linkages in this context.

The immunogens are prepared by coupling a hapten containing an —$NH_2$, —$CO_2H$, $CONHNH_2$, —CNOR, —CHO, —NCO, —NCS, —OCOCl or —OCSCl group to a poly(amino acid). The —$NH_2$ case can be coupled by activating the carboxylic acid group on the poly(amino acid) in the presence of the —$NH_2$ group. The activation of the carboxylic acid groups on the poly(amino acid) can be accomplished by mixing the hapten and the poly(amino acid) with 1-ethyl-3-(3-dimethylaminopropyl) carbodiimide (EDC), N,N'-dicyclohexylcarbodiimide (DCC), 1-cyclohexyl-3-(2-morpholinoethyl)carbodiimide metho-p-toluenesulfonate, or the like. The —$CO_2H$ case is also coupled by the activation method (EDC) or the active ester method. The —$CONHNH_2$ case is coupled in the same manner as for the non-aromatic amino case. The —CNOR case which is prepared from the corresponding cyano compound, is coupled directly to the poly(amino acid). The —CHO case is coupled to the poly(amino acid) by reductive amination. The poly(amino acid) is mixed with the —CHO hapten and the resulting imine is reduced with sodium cyanoborohydride to yield alkylated amines on the poly(amino acid). The isocyanate (—NCO) and isothiocyanate (—NSC) cases, which are prepared from the corresponding amino compound and chloroformate (—OCOCl) and chlorothioformate (—OCSCl) cases which are prepared from the corresponding alcohol compound, produce urea, thiourea, carbamate and thiocarbamate linkages, respectively. This is accomplished by direct coupling of the hapten to the poly(amino acid).

The synthesis of the above haptens (immunogen precursors) are accomplished in very similar ways. FIG. 21 shows an immunogen precursor class in accordance with a preferred embodiment of the method of the present invention.

In general, the hapten is prepared by reaction of the appropriate piperidine derivative with cyclohexanone in the presence of cyanide. The coupled product is then reacted with phenyl magnesium bromide to yield the hapten precursor. The hapten precursor is then converted into the hapten.

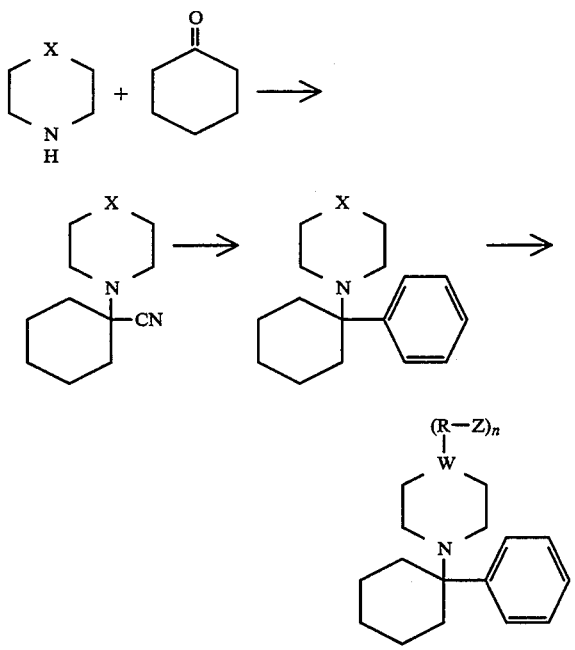

In the case where W is N, benzyl can be used as a protecting group. The benzyl group is removed after formation of the phencyclidine derivative. This secondary amine is a suitable hapten. It is possible to alkylate the amine with an alkyl halide (Cl, Br or I), e.g., bromoacetonitrile, 3-bromopropanol, 4-bromobutyric acid or the like, to prepare suitable haptens. It is also possible to form the chloroformamide derivative, which could make a suitable hapten, or form an amide derivative with an active ester, e.g., succinic anhydride, cyanoacetyl chloride or the like, containing a suitable group useful for coupling to a carrier protein. In the case where W is CH, X is CHOH, after formation of the phencyclidine derivative, a large variety of haptens may be prepared. The alcohol may be alkylated with an alkyl halide (Cl, Br, or I), containing a suitable group useful for coupling to a carrier protein, by standard procedures to form ether derivatives. The alcohol may be converted into the corresponding halogen derivative, such as, bromo, chloro or iodo, which will react with carbanion, alcohol or amine derivatives of compounds containing a suitable group for coupling to a carrier protein. The alcohol can be oxidized to the corresponding ketone which may be derivatized by known methods to a variety of compounds containing a suitable group useful for coupling to a carrier protein, e.g., Witrig reagents, alkoxyamine compounds, reductive amination with amino compounds or the like. Reductive amination of the ketone with ammonium acetate results in an amino derivative. The amino compound is suitable as a hapten or may be derivatized by known methods to a variety of hapten compounds analogous to the case where W is N and n is 0.

Nitrile derivatives (Z═CN) are converted to alkoxy imidates (Z═CNOR) by treating the nitrile with anhydrous alcohol and hydrogen chloride gas. The hydrazide derivatives (Z═CONHNH$_2$) are prepared from the corresponding carboxylic acid derivatives by active ester coupling with hydrazine or by reacting hydrazine with the corresponding carboxylic ester derivative.

Amines (Z═NH$_2$) are convertible to the isocyanate or thioisocyanate derivatives and alcohols (Z═OH) are convertible to chloroformate and chlorothioformate derivatives by reaction of the amine or the alcohol with phosgene or thiophosgene.

Aldehydes and ketones can be condensed with (aminohydroxy)alkylcarboxylic acids, such as NH$_2$OCH$_2$CO$_2$H, to produce substitued oxime derivatives. The oxime alkyl carboxylic acid derivatives can be partially reduced to the corresponding (aminohydroxy)alkylcarboxylic acid derivatives. The same type of condensation and reduction can be accomplished with hydrazine and hydrazine derivatives.

The Synthesis of the Tracers

Figure 14:
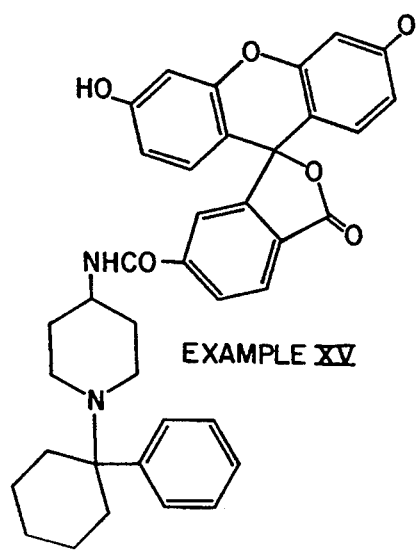

The tracers of the present invention are made by coupling a fluorescein moiety, or a derivative of fluorescein, to the general structure shown in FIGS. 2, 3 or 21 when Z is NH$_2$, COOH, CN or OH. The fluorescein moiety can be linked to the amino, carboxyl, imidate or alkoxy functional group by an amide, an amidine, a urea, a thiourea, a carbamate, a thiocarbonate, triazinylamino or sulfonylcarbamate linkage, as shown in FIG. 11. In the presently preferred embodiment, the fluorescein derivative is 6-carboxyfluorescein, and this is coupled to the precursor for 4-aminophencyclidine. Preferably, this reaction is performed in pyridine, but can also be perfomed in a co-solvent, e.g., methanol, dimethylsulfoxide, or the like, in the presence of a base, e.g., triethylamine or the like. The structure of the most preferred tracer is shown in FIG. 14. Useable tracers can be prepared from a variety of phencyclidine derivatives.

All phencyclidine derivatives that have a terminal amino group, such as amino, hydrazinyl, hydrazido or the like, are coupled to carboxyfluorescein by the active ester method or the mixed anhydride method, preferably the active ester method, and coupled to fluorescein isothiocyanate, DTAF or alkoxy DTAF by simply mixing the two materials in solution. The amino group can be converted to the isocyanate and thioisocyanate groups by reaction with phosgene and thiophosgene, respectively. These are then condensed with aminofluorescein to produce the tracer.

All phencyclidine derivatives that have a terminal carboxylic acid group, such as carboxylic acid, (aminohydroxy)alkylcarboxylic acid or the like, are coupled to aminofluorescein by the active ester method.

All phencyclidine derivatives that have a terminal hydroxy group can be coupled to fluorescein by reaction with DTAF, iodoacetamidofluorescein or fluorescein isothiocyanate in solution. The hydroxy group can be converted to the chlorosulfonylcarbamoyl, chloroformate and chlorothioformate groups by reaction with chlorosulfonylisocyanate, phosgene and thiophosgene, respectively. These derivatives are then coupled to aminofluorescein or aminomethylfluorescein in solution to produce the tracer.

All phencyclidine derivatives that have a terminal nitrile group are converted to imidates in anhydrous alcohol in the presence of hydrogen chloride gas. The imidate is then coupled to fluorescein amine or aminomethylfluorescein in solution to prepare the tracer.

The preparation of the various amino, carboxylic acid, hydroxy and nitrile derivatives of the anilide derivatives were described above in the immunogen preparation section.

The Assay

The particular tracer and antibodies of the present invention have been found to produce surprisingly good results in fluorescence polarization assays for phencyclidine and phencyclidine metabolites.

The assay of the present invention provides a more rapid phencyclidine and phencyclidine metabolite assay method than most prior art methods, because it requires no specimen treatment before analysis. The assay system accurately measures the presence or quantity of phencyclidine and phencyclidine metabolites in a sample, because antibody specificity precludes detection of compounds other than phencyclidine-like compounds.

The novel process of the present invention for determining the presence or amount of phencyclidine and phencyclidine metabolites in a sample comprises the steps Of:
(a) contacting a sample with:
  (1) phencyclidine antiserum, the phencyclidine antiserum containing monoclonal or polyclonal, preferably monoclonal, antibodies which have been raised against an immunogen having the structure shown in either FIG. 5 or 20, wherein W, R, Z, n and Q are as defined in the Summary of Invention; and
  (2) tracer compounds having the structure shown in either FIG. 5 or 20, wherein W, R, Z, n and Q are also as defined in the Summary of the Invention, with the tracer compound being capable of producing a detectable fluorescence polarization response to the presence of the phencyclidine antiserum;
(b) passing plane polarized light through the resulting solution from step (a) to obtain a fluorescence polarization response; and
(c) detecting the fluorescence polarization response of the solution of step (b) as a measure of the presence or amount of phencyclidine or phencyclidine derivatives in the sample.

The most preferred form of the process of the present invention employs monoclonal antibodies prepared against an immunogen having the structure shown in FIG. 23 with a tracer having the structure shown in FIG. 14.

In accordance with the method of the present invention for determining the presence or amount of phencyclidine and phencyclidine metabolites in a sample by a fluorescence immunoassay procedure using the tracer and immunogen compounds of the invention, a sample containing, or suspected of containing, phencyclidine and/or phencyclidine metabolites is mixed with: (1) a biologically acceptable salt of a tracer; and (2) a monoclonal or polyclonal, preferably monoclonal, antibody specific to phencyclidine and phencyclidine metabolites and to the tracer. The antibody is produced using the immunogen as described above. The phencyclidine and phencyclidine metabolites and tracer compete for limited antibody sites, resulting in the formation of complexes. By maintaining constant the concentration of tracer and antibody, the ratio of phencyclidine- and phencyclidine metabolites-antibody complex to tracer-antibody complex that is formed is directly proportional to the amount of phencyclidine and phencyclidine metabolites in the sample. Upon exciting the mixture with linearly polarized light and measuring the polarization (in units of millipolarization) of the fluorescence emitted by a tracer and a tracer-antibody complex, one is able to quantitatively determine the amount or qualitatively determine the presence of phencyclidine and phencyclidine metabolites in the sample.

The results can be quantified in terms of net millipolarization units and span (in millipolarization units). The measurement of net millipolarization units indicates the maximum polarization when a maximum amount of the tracer is bound to the antibody, in the absence of any phencyclidine or phencyclidine metabolites. The higher the net millipolarization units, the better the binding of the tracer to the antibody. The assay span is the difference between the net millipolarization values obtained when the maximum amount of tracer is bound in the absence of any phencyclidine and the net millipolarization obtained when a specific amount of phencyclidine or phencyclidine metabolites is present in the sample. A larger span allows for more millipolarization units to be placed between each of the calibrators of the standard curve generated for the assay, thereby providing better assay precision which, in turn, results in a better numerical analysis of the data obtained. The most preferred antibody-tracer combination has a span of at least 90 millipolarization units, but smaller spans may be used to produce acceptable assays. It is important to note that the span varies depending on the sample size used which, in turn, may alter the preferred combination.

Table I shows the results obtained with various embodiments of the tracers, antibodies and assay of the present invention, in terms of span and net millipolarization units at a sample size of 2 uL when the sample contains 75 ng/mL of phencyclidine. As seen from the data in Table I, an assay produced from an immunogen made from the hapten of FIG. 18 used in combination with the tracer of FIG. 13 and a 2 uL sample size provides good results. Accordingly, this combination of antibody and tracer is a preferred form of the invention for a sample size of 2 uL. However, the most preferred form of the assay of the present invention employs monoclonal antibodies prepared against an immunogen having the structure shown in FIG. 23 with tracers having the structure shown in FIG. 14. The antibody/tracer combinations represented by the combinations of FIGS. 18 and 12, FIGS. 18 and 14, FIGS. 18 and 15, and FIGS. 18 and 16 also produced acceptable results and are alternative preferred combinations.

TABLE I

Figure 12:
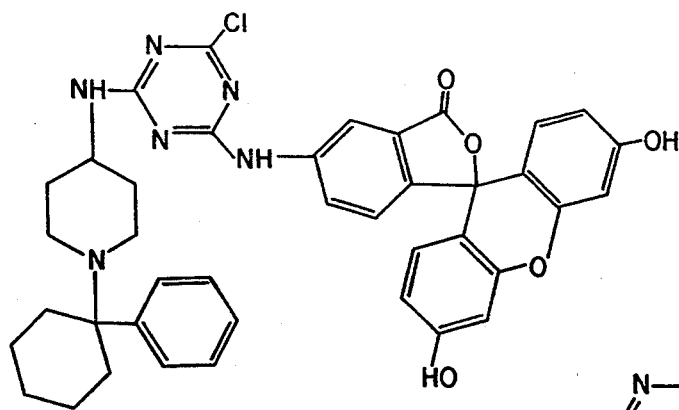
FIGS. 12 through 16 show various examples of structures of tracers in accordance with the present invention.
Figure 13:
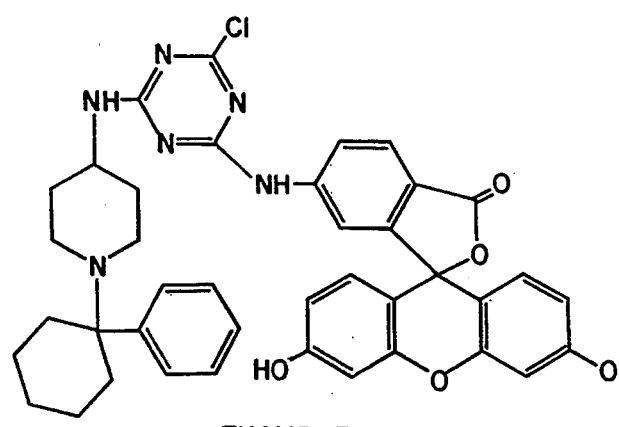
Figure 15:
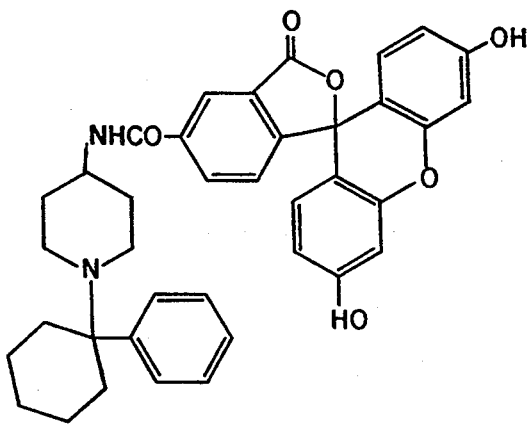
Figure 16:
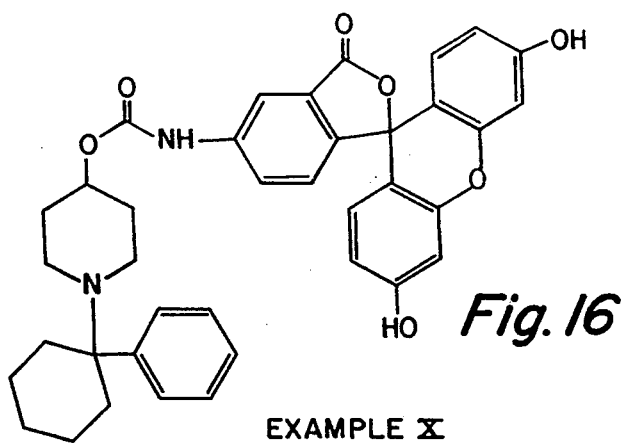
Figure 17:
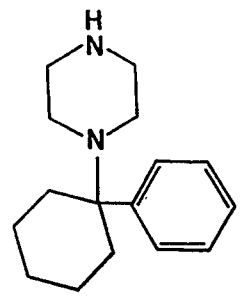
FIGS. 17 through 19 show various examples of structures of hapten reactants used to form the immunogens of the present invention.
Figure 18:
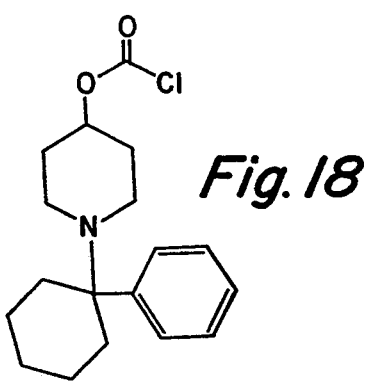
Figure 19:
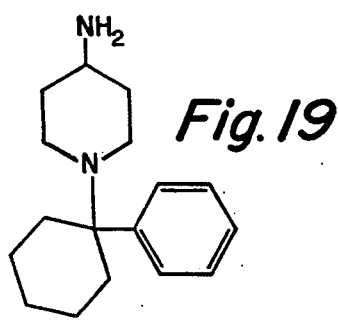

| Hapten used in Immunogen for Antibody | Tracer | Net Polarization* | Span** |
| --- | --- | --- | --- |
| FIG. 18 | FIG. 12 | 176 | 16 |
| FIG. 18 | FIG. 13 | 172 | 18 |
| FIG. 18 | FIG. 14 | 164 | 16 |
| FIG. 18 | FIG. 15 | 159 | 15 |
| FIG. 18 | FIG. 16 | 187 | 12 |
| FIG. 17 | FIG. 12 | 129 | 5 |
| FIG. 17 | FIG. 13 | 125 | 5 |
| FIG. 17 | FIG. 14 | 102 | 4 |
| FIG. 17 | FIG. 15 | 110 | 6 |
| FIG. 17 | FIG. 16 | 119 | 4 |
| FIG. 19 | FIG. 12 | 137 | 4 |
| FIG. 19 | FIG. 13 | 142 | 2 |
| FIG. 19 | FIG. 14 | 155 | 6 |
| FIG. 19 | FIG. 15 | 140 | 5 |
| FIG. 19 | FIG. 16 | 141 | 4 |

*In millipolarization units
**In millipolarization units at a phencyclidine concentration of 75 ng/ml and a 2 uL sample size.

Significant features of the most preferred combination of tracer and immunogen of the present invention, the combination of compounds having the structures shown in FIGS. 14 and 23 respectively, include: (1) the very high degree of specificity of the monoclonal antibodies generated against the immunogen for phencyclidine, phencyclidine metabolites and phencyclidine analogs; and (2) minimal cross reactivity of these antibodies to other drugs and to other naturally-occurring compounds.

Table II demonstrates the specificity of the monoclonal antibodies produced against an immunogen having the structure shown in FIG. 23 when compared with polyclonal antibodies of sheep and rabbits raised against the same immunogen. Crossreactivity to a panel of 10 different compounds was examined using antisera from sheep and rabbits and mouse monoclonal antibodies, all of which were raised against an immunogen having the structure shown in FIG. 23 and tested with the tracer of FIG. 14.

critical, provided a sufficient quantity is used to bind all free riboflavin in the sample.

At very high concentrations, phencyclidine and phencyclidine metabolites have a tendency to adhere to the plastic components of instrument probes. This results in the carryover of phencyclidine and phencyclidine metabolites from one sample to other samples. Standard dilution buffer, which contains 0.1M sodium phosphate, 0.01% bovine gamma globulin and 0.1% sodium azide, pH 7.5, is not sufficient to remove the phencyclidine and phencyclidine metabolites from the probe. Therefore, an aqueous solution of from about 40–60% (v/v) dimethylformamide, preferably 50%, from about 8–12% (v/v) n-butanol, preferably 10%, and from about 3–5% sodium chloride, preferably 4%, is preferably added to the kit as a wash solution.

The preferred method of the assay of the present invention will now be discussed in detail. The assay is a "homogeneous assay," which means that the end polarization readings are taken from a solution in which bound tracer is not separated from unbound tracer. This is a distinct advantage over heterogeneous immunoassay procedures, such as those where the bound tracer must be separated from the unbound tracer before a reading can be taken.

TABLE II

| Compound Added (100 ug/mL) | Concentration Found (ng/mL) | | | | | | Mouse Monoclonal |
|---|---|---|---|---|---|---|---|
| | Sheep | | Rabbits | | | | |
| | 630 | 631 | 2263 | 2264 | 2265 | 2266 | |
| Amitriptyline | 69 | 21 | 29 | 48 | 16 | 26 | 4 |
| Nortiptyline | 23 | 19 | 19 | 42 | 9 | 19 | Low |
| Imipramine | 37 | 25 | 26 | 49 | 19 | 28 | 3 |
| Desipramine | 32 | 22 | 19 | 34 | 15 | 19 | 2 |
| Dextromethorphan | 60 | 18 | 33 | 40 | 32 | Low | 31 |
| Ketamine | 23 | 36 | 25 | 51 | 8 | 13 | 3 |
| Promazine | 28 | 72 | 35 | 46 | 16 | 25 | 4 |
| Levallorphan | 31 | 49 | 62 | 73 | 27 | 27 | 16 |
| Cyclizine | 48 | 36 | 48 | 32 | 51 | 35 | 4 |
| Diphenhydramine | 30 | 24 | 31 | 39 | 25 | 25 | 1 |
| Span[1](mP) | 19 | 26 | 19 | 14 | 33 | 31 | 12 |
| Span[2](mP) | 80 | 101 | 78 | 100 | 149 | 90 | 78 |

Span[1] = The difference in net millipolarization readings obtained between a sample which contains 25 ng/ml of phencyclidine and a control sample which does not contain phencyclidine.
Span[2] = The difference in net millipolarization readings obtained between a sample containing no phencyclidine and the highest calibrator which contains 500 ng/ml phencyclidine. (This is also known as the dynamic range of the curve.)
Low = The result printed by the Abbott TD$_x$ ® Clinical Analyzer when the apparent concentration is less than the 0 calibrator.

The pH at which the method of the present invention is practiced must be sufficient to allow the fluorescein moiety of the tracers to exist in their open form. The pH may range from about 3 to 12, more usually in the range of from about 5 to 10, most preferably from about 6 to 9. Various buffers may be used to achieve and maintain the pH during the assay procedure. Representative buffers include borate, phosphate, carbonate, tris, barbital and the like. The particular buffer employed is not critical to the present invention, but the tris and phosphate buffers are preferred. The cation portion of the buffer will generally determine the cation portion of the tracer salt in solution.

Riboflavin binding protein (RBP) is added to the sample or to one or more of the assay reagents in order to bind any riboflavin present in the sample into RBP-riboflavin complexes, thus eliminating potential fluorescence interference. RBP is a protein of approximately 32,000 M.W. which is isolated from egg whites. Upon isolation from the egg, each molecule of RBP contains one molecule of riboflavin. This, the holoprotein form of RBP, must be converted to the apoprotein form by dialysis, under acidic conditions, to remove the bound riboflavin. The RBP apoprotein utilized in the present invention is commercially available from Sigma Chemical Company, St. Louis, Mo. The amount used is not The reagents for the fluorescence polarization assay of the present invention comprise: (1) monoclonal or polyclonal antibodies for phencyclidine and phencyclidine metabolites; and (2) tracer reagent. Monoclonal antibodies are the preferred antibodies for use in the assay of the present invention. The most preferred antibodies for use in this assay are monoclonal antibodies generated against an immunogen having the structure shown in FIG. 23.

Additionally, largely conventional solutions including a pretreatment solution, a dilution buffer, phencyclidine calibrators and phencyclidine controls are desirably prepared. Typical solutions of these reagents, some of which are described below, are commercially available in assay "kits" from Abbott Laboratories, Abbott Park, Ill.

All percentages expressed herein are weight/volume unless otherwise indicated. The tracer formulation presently preferred is 164 nanomolar tracer in: 0.1 molar tris buffer at pH 7.9; 10% sodium cholate; 0.1% sodium azide; and 0.01% bovine gamma-globulin. The antiserum formulation comprises mouse monoclonal antibody diluted with: 0.05 molar HEPES buffer at pH 7.5; 0.1% sodium azide; 1.0% ovalbumin; and 10% glycerol (volume/volume). The dilution buffer comprises: 0.1 molar sodium phosphate at pH 7.5; 0.1% sodium azide; and 0.01% bovine gamma-globulin. The pretreatment solution comprises: 0.01% bovine gamma-globulin; 0.1 molar tris buffer at pH 7.5; 0.1% sodium azide; and 10mg/mL riboflavin binding protein. An aqueous wash solution employed to wash the probe of an automated or semiautomated instrument used to conduct the assay, contains 50% (v/v) dimethylformamide, 10% (v/v) n-butanol and 4% sodium chloride. Phencyclidine calibrators comprising phencyclidine in normal human urine at concentrations of 0.0, 25.0, 60.0, 120.0, 250.0, and 500.0 nanograms per milliliter, with 0.1% sodium azide as a preservative are useful. Phencyclidine controls comprising phencyclidine in normal human urine are provided at concentrations of 35.0, 100.0 and 250.0 nanograms per milliliter with 0.1% sodium azide as a preservative are also useful.

The preferred procedure is especially designed to be used in conjunction with the Abbott TD$_x$® Clinical Analyzer or the Abbott AD$_x$® Drugs of Abuse System, both of which are available from Abbott Laboratories, Abbott Park, Ill. Fifty microliters of urine is required. The calibrators, controls, or unknown samples are pipetted directly into the sample well of the TD$_x$® sample cartridge. One of the advantages of this procedure is that the sample does not require any special preparation. The assay procedure from this point is fully automated.

If a manual assay is being performed, the sample is mixed with the pretreatment solution in dilution buffer and a background reading is taken. The tracer is then mixed with the assay. The antibody is then finally mixed into the test solution. After incubation, a fluorescence polarization reading is taken.

The fluorescence polarization value of each calibrator, control or sample is determined and is printed on the output tape of an instrument, such as the Abbott TD$_x$® Analyzer or AD$_x$® System. A standard curve is generated in the instrument by plotting the polarization of each calibrator versus its concentration using a nonlinear regression analysis. The concentration of each control or sample is read off of the stored calibration curve and printed on the output tape.

With respect to the foregoing preferred procedure, it should be noted that the tracer, antibody, pretreatment solution, wash solution, calibrators and controls should be stored between about 2° C. and about 8° C. while the dilution buffer should be stored at ambient temperature. A standard curve and controls should be run every two weeks, with each calibrator and control run in duplicate. All samples can be run in duplicate.

A significant feature of the most preferred assay of the present invention, one which employs a monoclonal antibody prepared against an immunogen having the structure shown in FIG. 23 and a tracer having the structure shown in FIG. 14, is the high degree of specificity to phencyclidine, phencyclidine metabolites and phencyclidine analogs, while greatly minimizing cross-reactivity to a host of other synthetic and naturally-occuring compounds. Representative crossreactivity data for phencyclidine metabolites and phencyclidine analogs employing the assay of the present invention wherein the tracer has the structure shown in FIG. 14 and the antibodies have been raised against an immunogen having the structure shown in FIG. 23 are shown in Table 3(a) below. The four columns indicate the following information:

(1) Column 1—Indicates the particular compound assayed for;
(2) Column 2—Indicates the amount of the test compound added to drug-free urine;
(3) Column 3—Indicates the amount of test compound found in the resulting urine;
(4) Column 4—Indicates the percent crossreactivity.

The percent cross-reactivity value presented in column four was obtained by the following mathematical formula:

$$\text{Percent Cross-Reactivity} = 100 \times \frac{\text{Concentration of Test Compound Detected in the Resulting Human Urine}}{\text{Concentration of Test Compound Added to Normal Drug-Free Human Urine}}$$

TABLE 3 (a)

| 1 | 2 | 3 | 4 |
|---|---|---|---|
| 4-OH pip Phencyclidine (PCP metabolite) | 100,000 | HI | NR |
|  | 10,000 | HI | NR |
|  | 1,000 | 148.33 | 14.8 |
|  | 100 | 16.68 | 16.7 |
|  | 50 | 7.80 | 15.6 |
|  | 25 | 5.59 | 22.4 |
| 1-Phenylcyclohexylamine (PCP metabolite) | 100,000 | ND | — |
| N-Ethyl-1-Phenylcyclo-hexylamine (PCP analog) | 100,000 | 139.77 | 0.1 |
|  | 10,000 | 19.75 | 0.2 |
|  | 1,000 | ND | — |
| 1-(1-Phenylcyclohexyl)-pyrrolidine (PCPy) (PCP analog) | 1,000 | HI | NR |
|  | 100 | 84.98 | 85.0 |
|  | 50 | 43.72 | 87.4 |
|  | 25 | 21.37 | 85.5 |
| 1-[1-(2-Thienyl)Cyclohexyl]-morpholine (TCM) (PCP analog) | 1,000 | 185.55 | 18.6 |
|  | 100 | 25.33 | 25.3 |
|  | 50 | 13.23 | 26.5 |
|  | 25 | 7.11 | 28.4 |
| 1-[1-(2-Thienyl)Cyclohexyl]-piperidine (TCP) (PCP analog) | 1,000 | 467.17 | 46.7 |
|  | 100 | 55.57 | 55.6 |
|  | 50 | 30.25 | 60.5 |
|  | 25 | 14.74 | 59.0 |
| 1-[1-(2-Thienyl)Cyclohexyl]-pyrrolidine (TCPy) (PCP analog) | 1,000 | 377.63 | 37.8 |
|  | 100 | 46.26 | 46.3 |
|  | 50 | 23.46 | 46.9 |
|  | 25 | 12.66 | 50.6 |

NR = Not Reported.
ND* = None Detected: Concentration less than the sensitivity of the assay (5.00 ng/mL).
HI = The result printed by the Abbott TD$_X$® Clinical Analyzer when the concentration is greater than the highest calibrator.

Another advantage of the assay of the present invention is the low cross-reactivity of the assay with non-phencyclidine compounds. Representative cross-reactivity data which indicate a low cross-reactivity of the assay for compounds which have a similar chemical structure to phencyclidine are shown in Table 3(b) (for a tracer having the structure shown in FIG. 14 and monoclonal antibodies generated against an immunogen having the structure shown in FIG. 23). The four columns in Table 3(b) indicate the same information as is described above for Table 3(a).

TABLE 3 (b)

| 1 | 2 | 3 | 4 |
|---|---|---|---|
| Dextromethorphan | 100,000 | 20.79 | <0.1 |
|  | 10,000 | ND* | — |
| Fencamfamine | 1,000,000 | 20.58 | <0.1 |
|  | 100,000 | ND* | — |
| Levallorphan | 100,000 | 6.02 | <0.1 |
|  | 50,000 | ND* | — |

TABLE 3 (b)-continued

| 1 | 2 | 3 | 4 |
|---|---|---|---|
| Phenyltoloxamine | 1,000,000 | 7.72 | <0.1 |
|  | 100,000 | ND* | — |
| Picenadol | 1,000,000 | 15.04 | <0.1 |
|  | 100,000 | ND* | — |
| Prolintane | 100,000 | 15.66 | <0.1 |
|  | 10,000 | ND* | — |
| Thioridazine | 1,000,000 | 34.23 | <0.1 |
|  | 100,000 | ND | — |

ND* = None Detected: Concentration less than the sensitivity of the assay (5.00 ng/mL).

In addition, the compounds presented in Table 3(c) showed crossreactivity results less than 5.0 ng/mL when tested at 100 ng/mL.

TABLE 3 (c)

Acetaminophen
Acetopromazine
N-Acetyl-1-cysteine
Acetylsalicylic Acid
Allobarbital
Alpha-methyl-1-DOPA
Alphaprodine
Alphenal
Alprazolam
Alprenolol
Amantadine
Aminoglutethimide
Aminopyrine
*Amitriptyline
cis-10-OH-Amitriptyline
trans-10-OH-Amitriptyline
Amobarbital
Amoxicillin
d,1-Amphetamine
p-OH-Amphetamine
Amphotericin
Ampicillin
Anileridine
Antabuse
*Apomorphine
Aprobarbital
Aspartame
Atenolol
Atropine
*Azatadine
Barbital
Barbituric Acid
Beclomethasone
Benactyzine
Benzocaine
Benzioc Acid
Benzoylecgonine
Benztropine
Benzylpenicillin
Brallobarbital
Bromocriptine
Brompheniramine
Bupivacaine
Buprenorphine
Buspirone
Butabarbital
Butethal
Butorphanol
Butyrophenone
Caffeine
Calcium Hypochlorite
Carbamazepine
Ephedrin
Epinephrine
Erythromycin
Estradiol
Estriol
Estrone-3-sulfate
Ethambutol
Ethinamate
4-Ethyl-2,5-dimethoxy-amphetamine (DOET)
Carbamazepine-10,11-epoxide
Carisoprodol
Carphenazine
Cephalexin
Cephaloridine
*Chloral Hydrate
Chloramphenicol
Chlordiazepoxide
Chloroquine
Chlorothiazide
*Chlorpheniramine
Chlorpromazine
Chlorpropamide
Chlorzoxazone
Cholesterol
Cimetidine
Ciprofloxacin
Clemastine
Clindamycin
Clomipramine
Clonidine
Cocaine
Codeine
Cortisone
β-Cortol
Cyclizine
Cyclobarbital
Cyclobenzaprine
Cyproheptadine
Deoxycorticosterone
Desipramine
Diacetylmorphine
Diazepam
Dibenzepin
Dibucaine
Diethylpropion
Diflunisal
Digitoxin
Digoxin
Dihydrocodeine
Dihydromorphine
10,11-Dihydroxy-carbamazepine
Diltiazem
1,3-Dimethylbarbituric Acid
*Diphenhydramine
Diphenoxylate
Diphenylhydantoin
Dopamine
Dothiepin
*Doxepin
*Doxylamine
Ecgonine
Levothyroxine
Lidocaine
*Loperamide
Loratadine
*Lorazepam
Loxapine
LSD
Maprotiline
Mazindol
Mefenamic Acid
Ethylmorphine
Fencamfamine
*Fenfluramine
Fenoprofen
Fentanyl
Flufenamic Acid
*Fluoxetine
Fluphenazine
*Flurazepam
Flurbiprofen
Furosemide
Gentisic Acid
Glutethimide
Glycopyrrolate
*Guaiacol Glyceryl Ether
Haloperidol
Hexobarbital
Hippuric Acid
Histamine
Hydralazine
Hydrochlorothiazide
Hydrocodone
Hydrocortisone
Hydromorphone
5-Hydroxyindole-3-acetic Acid
5-Hydroxyindole-2-carboxylic Acid
5-(p-Hydroxyphenyl)-5-phenylhydantoin (HPPH)
Hydroxyzine
*Ibuprofen
*COOH-Ibuprofen
*OH-Ibuprofen
Iminostilbene
Imipramine
Indole-3-acetic Acid
Indole-3-butyric Acid
Indomethacin
Iproniazid
Isoproterenol
Isoxsuprine
*Ketamine
Ketoprofen
Labetalol
Levorphanol
Nicotine
Nicotinic Acid
Nifedipine
p-Nitrophenol
Nomifensine
Norchloriazepoxide
*N-Norcodeine
Nordoxepin
Norethindrone
*N-Normorphine
N-Noroxymorphone
N-Norpropoxyphene
Nortriptyline
cis-10-OH-Nortriptyline
trans-10-OH-Nortriptyline
Nylidrin
Octopamine
Opipramol
Orotic Acid
*Orphenadrine
Oxazepam
*Oxycodone
Oxymetazoline
*Oxmorphone
Oxyphenbutazone
Pemoline
Penicillin G
Pentazocine
Pentobarbital
Perphepazine
Phenacetin
*Phendimetrazine
Phenelzine
Phenethylamine
Phenformin
Pheniramine
Phenmetrazine
Melanin
Meperidine
Mephenytoin
Mepivacaine
Meprobamate
Mescaline
Methadone
Methadone Primary Metabolite
d-Methamphetamine
d,1-Methamphetamine
Methapyrilene
Methaqualone
Metharbital
Methocarbamol
Methotrimeprazine
Methoxyphenamine
Methoxypromazine
Methsuximide
4-Methyl-2,5-dimethoxy-amphetamine (DOM)
3,4-Methylenedioxy-amphetamine (MDA)
3,4-Methylenedioxy-N-ethyl-amphetamine (MDE)
3,4-Methylenedioxy-methamphetamine (MDMA)
*Methylphenidate
Methyprylon
*Metoclopramide
Metoprolol
Metronidazole
Midazolam
6-Monoacetylmorphine
Monoethylglycinexylidide (MEGX)
*Morphine
Morphine-3β-D-glucuronide
Nafcillin
Nalbuphine
Nalorphine
Naloxone
Naltrexone
Naoroxen
Niacinamide
Procainamide
Procaine
Prochlorperazine
Progesterone
Promazine
Promethazine
Propoxyphene
Propranolol
*Propylhexedrine
Protriptyline
Pseudoephedrine
*Pyrilamine
Quinidine
Quinine
*Ranitidine
Salicylic Acid
Scopolamine
Secobarbital
Serotonin
Strychnine
Sudoxicam
Sulfamethazine
Sulfamethoxazole
Sulfathiazole
Sulindac
Terbutaline
Terfenadine
Testosterone
Tetracaine
Tetracycline
**11-Nor-delta-9-tetrahydro-cannabinol-9-carboxylic-Acid
Tetrahydrocortisone
Tetrahydrozoline
Thebaine
*Thenyldiamine
Theophylline ferred assay of the invention in comparison with RIA and GC/MS.

TABLE 4 (a)

| | N | TDx POS/NEG | ADx POS/NEG | EMIT POS/NEG | GC/MS POS/NEG |
|---|---|---|---|---|---|
| <25 ng/ml by TDx | 101 | 0/101 | 0/101 | 0/101 | 0/2 99 NT |
| ≧25 ng/ml by TDx | 98 | 98/0 | 98/0 | 95/3* | 98/0 |

*See Table Below

| SAMPLE # | TDx (ng/mL) | ADx (ng/mL) | EMIT POS/NEG | GC/MS (ng/mL) |
|---|---|---|---|---|
| 11 | 40.25 | 40.4 | NEG | 39 |
| 60 | 59.07 | 59.4 | NEG | 41 |
| 79 | 45.99 | 47.6 | NEG | 39 |

TABLE 4 (b)

| | N | TDx POS/NEG | ADx POS/NEG | RIA POS/NEG | GC/MS POS/NEG |
|---|---|---|---|---|---|
| <25 ng/ml by TDx | 100 | 0/100 | 0/100 | 0/100 | 100 NT |
| ≧25 ng/ml by TDx | 101 | 101/0 | 100/1* | 101/0 | 101/0 |

*See Table Below

| SAMPLE # | TDx (ng/mL) | ADx (ng/mL) | RIA POS/NEG | GC/MS (ng/mL) |
|---|---|---|---|---|
| 152 | 26.32 | 24.9 | POS | 26 |

NT = NOT TESTED
"POSITIVE" by the TDx and ADx Instruments = Concentration greater than or equal to the threshold, which is 25 ng/mL phencyclidine.
"POSITIVE" by RIA = Counts per minute less than or equal to the threshold, which is 25 ng/mL phencyclidine.
"POSITIVE" by EMIT = Absorbance rate greater than or equal to the EMIT Low Calibrator, which is 75 ng/mL phencyclidine.
"POSITIVE" by GC/MS = Concentration greater than or equal to 25 ng/mL phencyclidine.

| | |
|---|---|
| Phenobarbital | Thiopropazate |
| Phenothiazine | Thiothixene |
| *Phentermine | Tolbutamide |
| Phenylbutazone | Tranylcypromin |
| Phenylpropanolamine | Trazodone |
| Phenytoin | Triamterene |
| Piperacetazine | Trifluoperazine |
| 1-Piperidinocyclohexane Carbonitrile | Trihexphenidyl Trimethoprim |
| Piroxicam | Trimipramine |
| Potassium Chloride | *Tripelennamine |
| Prazosin | Triprolidine |
| Preunisolone | Tropic Acid |
| Preunisone | Tropine |
| Pregnenolone | Tryptamine |
| Prilocaine | Tyramine |
| Primidone | Uric Acid |
| Probenecid | Warfarin |
| | Zomepirac |
| | Amoxapine |
| | Nialamide |
| | Naphazoline |

*Tested at 1,000 ug/mL
**Tested at 10 ug/mL

The assay of the present invention was also compared to other methods for the detection of phencyclidine, such as gas chromatography/mass spectrometry (GC/MS), radioimmunoassay (RIA) and enzyme multiplied immunoassay technology (EMIT) by testing drug-free urine specimens and urine specimens containing phencyclidine and phencyclidine metabolites with each of these methods. Representative data are presented: (1) in Table 4(a) below for the most preferred assay of the present invention, which employs a tracer having the structure shown in FIG. 14 and monoclonal antibodies raised against an immunogen having the structure shown in FIG. 23, in comparison with EMIT and GC/MS; and (2) in Table 4(b) below for the most pre- It should be understood that the foregoing detailed description and the following Examples are intended to be illustrative, but not limiting, with respect to the scope of the present invention. Various modifications will become apparent to one skilled in the art, and thus it is intended that the scope of the invention be defined solely by the claims and legal equivalents thereof.

EXAMPLES

Examples I through III and XVII are directed to preparation of an immunogen useful for producing antibody; Examples IV through IX, XI and XII are directed to the synthesis of precursors for immunogens and tracers; Examples X and XIII through XVI are directed to the preparation of tracers; and Example XVIII describes an experiment during which monoclonal antibodies were prepared against an immunogen having the structure shown in FIG. 23.

Example I 1-(1-phenylcyclohexyl)piperazine Immunogen 1-(1-phenylcyclohexyl)piperazine (25 mg) in 2 mL 50% methanol/water was added to bovine serum albumin (30 mg) in 2 mL distilled water with stirring. The pH was adjusted to 5.5 with 0.1N HCl. 1-ethyl-3-(3-dimethylaminopropyl)carbodiimide (1 g) in 2 mL distilled water was added in four parts adjusting the pH with 0.1N HCl after each addition to about pH 5.5. The mixture was then stirred at room temperature for 18 hours. The mixture was dialysed in a cellulose dialysing tube (Spectra/Por ®, MW 12,000–14,000) against distilled water for four days. The solution from the dialysing tube was found to contain 2.7 mg/mL protein via the Biuret protein concentration determining method.

Example II 4-(1-(1-phenylcyclohexyl)) piperidinyl chloroformate Immunogen 4-(1-(-phenylcyclohexyl)) piperidinyl chloroformate (57 mg) in 0.25 mL dimethylformamide was added to bovine serum albumin (50 mg) in 2.5 mL 0.1M phosphate buffer, pH 8.0, and stirred at room temperature for one hour. The mixture was dialysed in a cellulose dialysing tube (Spectra/Por®, MW 12,000–14,000) against distilled water for 2 days and 0.90% saline for one day. The solution from the dialysing tube was found to contain 15.4 mg/mL protein via the Biuret protein concentration determining method.

Example III 4-amino-1-(1-phenylcyclohexyl) piperidine Immunogen 4-amino-1-(1-phenylcyclohexyl) piperidine (40 mg) in 2.5 mL dimethylformamide and 7.5 mL distilled water was added to bovine serum albumin (69.5 mg) in 2.0 mL distilled water with stirring and the pH was adjusted to pH 5.0–5.5 with 0.1N HCl. 1-ethyl-3-(3-dimethylaminopropyl)carbodiimide (60 mg) was added while maintaining the pH at 5.0–5.5 with 0.1N HCl. The mixture was stirred at room temperature for 2 hours. The mixture was dialysed in a cellulose dialysing tube (Spectra/Por®, MW 12 000–14 000) against distilled water for 3 days. The solution from the dialysing tube was found to contain 4.19 mg/mL protein via the Biuret protein concentration determining method.

Example IV 1-benzyl-4,(1-cyanocyclohexyl) piperazine 1-benzylpiperazine (Aldrich Chemical Co., Inc., supra) (6.12 g) was dissolved in 10 mL deionized water and cooled to 0° C. Concentrated hydrochloric acid (3.6 mL) was added to adjust the pH to 5.After warming to room temperature, 3.6 mL cyclohexanone was added, followed by potassium cyanide (2.4 g) in 6 mL deionized water. The solution slowly became cloudy. After 18 hours, the solid was filtered. The solid was dissolved in chloroform, dried over $Na_2SO_4$, filtered and the solvent was removed in vacuo to yield pure 1-benzyl-4-(1-cyanocyclohexyl) piperazine.

Example V 1-benzyl-4-(1-phenylcyclohexyl) piperazine

To bromobenzene (0.6 g) and magnesium turnings (0.2 g) in 30 mL dry tetrahydrofuran under nitrogen was added a small crystal of iodine and 10 drops of 1,2-dibromoethane. After small bubbles began to form, the reaction was stirred and heated to reflux for 4 hours. After cooling to room temperature, 1-benzyl-4-(1-cyanocyclohexyl)piperazine (1 g) was added. After 23 hours, the reaction was filtered, 20 mL saturated aqueous ammonium chloride was added and the mixture was extracted with diethyl ether. The ether was dried and removed in vacuo. The residue was chromatographed on silica gel eluted with chloroform to yield pure 1-benzyl-4-(1-phenylcyclohexyl)piperazine.

Example VI 1-(1-phenylcyclohexyl)piperazine 1-benzyl-4-(1-phenylcyclohexyl)piperazine (0.47 g) was dissolved in 86 mL methanol and 14 mL 0.2N HCl in methanol. The mixture was hydrogenated over palladium black (0.1175 g) and 3 atm. of hydrogen at room temperature for 1 hour. The reaction was filtered and the solvent was removed in vacuo. The residue was chromatographed on silica gel eluted with the appropriate mixture of methanol and chloroform to yield pure 1-(1-phenylcyclohexyl)piperazine.

Example VII 1-(1-cyanocyclohexyl)-4-hydroxyl piperidine 4-hydroxypiperidine (Aldrich Chemical Co., Inc., supra) (5 g) was dissolved in distilled water (14 mL), cooled to 0° C. and the pH was adjusted to between 4 and 5 by addition of concentrated hydrochloric acid and 4-hydroxypiperidine. After warming to room temperature, 5.2 mL cyclohexanone and 3.3 g potassium cyanide in water (9 mL) were added sequentially. After 18 hours of stirring at room temperature, the solid was filtered. The solid was dissolved in 100 mL methylene chloride, dried over $Na_2SO_4$, filtered and the solvent was removed in vacuo to yield pure 1-(1-cyanocyclohexyl)-4-hydroxypiperidine.

Example VIII 1-(1-phenylcyclohexyl-4-hydroxypiperidine

To bromobenzene (4.1 mL) and magnesium turnings (4 g) in 200 mL dry tetrahydrofuran under nitrogen was added a crystal of iodine and 10 drops of 1,2-dibromoethane. After small bubbles began to form, the reaction was stirred and heated to reflux for 4 hours. After cooling to room temperature 1-(1-cyanocyclohexyl)-4-hydroxypiperidine (2 g) was added. After 17 hours, the reaction was filtered, 120 mL saturated ammonium chloride was added and the mixture was extracted with ethyl ether. The ether layer was dried and the solvent was removed in vacuo. The residue was chromatographed on silica gel eluted with the appropriate mixture of methanol and chloroform to yield pure 1-(1-Phenylcyclohexyl)-4-hydroxypiperidine.

Example IX 4-(1-(1-phenylcyclohexyl))piperidinyl chloroformate 1-(1-Phenylcyclohexyl)-4-hydroxypiperidine (0.261 mg) was suspended in 5 mL dry benzene and 2 mL 10% phosgene in benzene was added. After stirring, and then stoppering for 3 hours at room temperature, 1 mL of chloroform was added. After 30 minutes, the solvent was removed in vacuo. Carbon tetrachloride (dry) (1 mL) was added and removed in vacuo to yield 4-(1-(1-phenyl cyclohexyl))piperidinyl chloroformate as a white solid.

Example X 4-(5-fluoresceinylcarbamoyl)-1-(phenylcyclohexyl) piperidine 4-(1-(1-phenylcyclohexyl))piperidinyl chloroformate (10 mg) and 5-aminofluorescein (10 mg) were dissolved in 2 mL dry pyridine and stirred at room temperature for about 18 hours. The reaction was chromatographed on silica gel preparative plates eluted with the appropriate ratio of methanol, chloroform and acetic acid to yield the desired tracer.

Example XI

1-(1-phenylcyclohexyl)-4-piperidone 1-(1-phenylcyclohexyl) -4-hydroxypiperidine was dissolved in 15 mL glacial acetic acid and 0.3 mL concentrated sulfuric acid, and 1.9 mL Jones reagent (made from 26.72 g $H_2CrO_4$ and 23 mL $H_2SO_4$ diluted to 100 mL with water) was added dropwise. After stirring at room temperature for 20 minutes, 2 mL 2-propanol, Zn(Hg) (made from 1.5 g mossy zinc and 0.2 g mercuric chloride in 20 mL water and 0.25 mL concentrated hydrochloric acid at room temperature for 5 minutes), sodium citrate dihydrate (3.6 g) and 35 mL deionized water were added sequentially. After stirring the solution at room temperature for 30 minutes, the reaction was extracted with chloroform. The solvent was removed in vacuo. Distilled water was added and removed in vacuo. The residue was chromatographed on silica gel eluted with the appropriate mixture of methanol and chloroform to yield pure 1-(1-phenylcyclohexyl)-4-piperidone.

Example XII

4-amino-1-(1-phenylcyclohexyl)piperidine 1-(1-phenylcyclohexyl)-4-piperidone (0.245 g) and ammonium acetate (1 g) were dissolved in 3.5 mL dry methanol. After stirring at room temperature for 10 minutes, sodium cyanoborohydride (0.1 g) was added and the reaction was stoppered. After 20 hours, 0.1 mL of concentrated hydrochloric acid was added followed by 10 mL water and the mixture was stirred for 1.5 hours. The solution was basified with potassium carbonate to pH 9 and extracted with methylene chloride. The methylene chloride was dried over $Na_2SO_4$ and removed in vacuo. The product distilled as a colorless, clear oil at 90–130° C. in vacuo (about 5 mmHg).

Example XIII

4-(4-chloro-6-(5-fluoresceinylamino)-1,3,5-triazin-2-yl) amino-1-(1-phenylcyclohexyl)piperidine 4-amino-1-(1-phenylcyclohexyl)piperidine (9 mg) and 5-((4,6-dichloro-1,3,5-triazin-2-yl)amino) fluorescein (17 mg) were dissolved in 1 mL methanol and 0.1 ml triethylamine. After stirring at room temperature for 30 hours, the solvent was removed in vacuo. The residue was chromatographed on silica gel preparative plates eluted with the appropriate mixture of methanol and chloroform to yield the tracer.

Example XIV

4-(4-chloro-6-(6-fluoresceinylamino)-1,3,5-triazin-2-yl) amino-1-(1-phenylcyclohexyl)piperidine The same procedure was used as in Example XIII except that 6-((4,6-dichloro-1,3,5-triazin-2-yl)amino) fluorescein was used instead of 5-((4,6-dichloro-1,3,5-triazin-2-yl)amino)fluorescein.

Example XV

4-(fluorescein-6-ylcarbonyl)amino-1-(1-phenycyclohexyl) piperidine 6-carboxyfluorescein (Calbiochem, La Jolla, Calif.) (14 mg), N-hydroxy succinimide (6 mg) and N,N'-dicyclohexyl-carbodiimide (14 mg) were dissolved in 0.5 mL dry pyridine and stirred at room temperature, and then stoppered. After 1 hour, 4-amino-1-(1-phenylcyclohexyl) piperidine (9 mg) was added followed by 0.5 mL dry pyridine. After 15 hours, the reaction was chromatographed on silica gel preparative plates eluted with the appropriate mixture of methanol, chloroform and acetic acid.

Example XVI

4-(fluorescein-5-ylcarbonyl) amino-1-(1-phenycyclohexyl)piperidine

The same procedure was used as in Example XV except that 5-carboxyfluorescein (Calbiochem, supra) was used instead of 6-carboxyfluorescein.

Example XVII

N-[3-hydroxymethylpiperidino]cyclohexyl carbonitrile (Preparation of the Most Preferred Immunogen—FIG. 23)

A solution of 1.00 g (8.68 mmol) of 3-hydroxymethylpiperidine in a mixture of 8 mL absolute ethanol and 8 mL water was cooled to 0° C., and acidified to pH 3–4 with concentrated hydrochloric acid. Subsequently, 0.83 mL (8.04 mmol) cyclohexanone and 550 mg (8.43 mmol) potassium cyanide were added, and the resulting mixture was tightly stoppered and stirred overnight at ambient temperature. The reaction mixture was concentrated on a rotovap, basified to pH 8–9 with sodium hydroxide, and extracted 3×30 mL with chloroform. The extracts were dried over sodium sulfate and concentrated. Chromatography on a silica gel column, with 5% methanol/chloroform as eluent, produced 1.268 g of a pale yellow oil.

1-[N-[3-hydroxymethylpiperidino]]-1-phenylcyclohexane

To a solution of 563 mg (2.54 mmol) of the oil prepared in the preceding experiment in 15 mL tetrahydrofuran, cooled to 0° C., was added 5.08 mL (3.0M, 15.2 mmol) phenylmagnesium bromide. The solution was stirred for 5 minutes, and warmed to 55° C. for 2.5 hours. After it was allowed to cool, it was stirred for 12 hours at ambient temperature. The reaction was quenched with water and ammonium chloride, and extracted 3×30 mL with ethyl acetate. The combined extracts were dried over sodium sulfate and concentrated. Chromatography on a silica gel column, eluting with 10% methanol/chloroform, produced 365 mg of a clear colorless oil.

1-[N-(3-carboxypiperidino)]-1-phenylcyclohexane

To a solution of 150 mg (0.55 mmol) of the alcohol prepared in the preceding experiment in 5.5 mL glacial acetic acid cooled to 0° C. was added a solution of 137 mg (1.38 mmol) of chromium trioxide in a mixture of 1.5 mL glacial acetic acid and 1.0 mL of water. The reaction was warmed to ambient temperature and stirred for 5 hours. Most of the acetic acid was removed by rotary evaporation, and the residue was diluted in water, basified to pH 7–8 with 1M NaOH, and extracted 5 ×15 mL with chloroform. The combined extracts were dried over sodium sulfate and concentrated. Chromatography on silica gel, with 8% methanol/chloroform as eluent, produced, in addition to some impure product, 66 mg of a clear colorless oil.

Linkage of Hapten to Protein Carrier

Sixty milligrams ($1.05 \times 10^{-4}$ moles) of 1-[N-(carboxypiperidino)]-1-phenylcyclohexane was dissolved in 2.0 mL of dimethylsulfoxide. To this solution was added $1.74 \times 10^{-4}$ moles each of N-hydroxysuccinimide and dicyclohexylcarbodiimide. The mixture was stirred for two hours at room temperature. The solution containing the active ester was then added to a rapidly stirring solution of 100 mg bovine thyroglobulin dissolved in 37 mL of DMSO: 0.05N sodium phosphate (1:1) with a final pH of 8.5. The mixture was stirred overnight at room temperature and subsequently dialyzed against 60% DMSO for 8 hours. During the following dialysis, the DMSO was reduced to 25%. The final three dialysis changes were 0.05M sodium phosphate buffer at pH 7.5. The resulting fluffy white precipitate was removed from the dialysis bag and harvested by centrifugation. The pellet containing the precipitate was resuspended in a minimum amount of buffer and used as the immunogen in Example XVIII.

Example XVIII

Preparation of Monoclonal Antibodies Against an Immunogen having the Structure shown in FIG. 23

(Most Preferred Antibodies)

Six week old female BALB/c mice were immunized intraperitoneally with 100 ug of an immunogen having the structure shown in FIG. 23 mixed 1:1 in RIBI adjuvant (RIBI Immunochem, Hamilton, Mont.) into two different sites in the ventral rear peritoneal cavities during weeks 1, 5, 9 and 16.

In order to determine whether or not the antibodies produced by the immunized mice are specific for phencyclidine and phencyclidine metabolites, a competitive binding immunoassay is run by adding free phencyclidine to the sample. The free phencyclidine will compete with the tracer for the binding sites on the antibody. If the free phencyclidine binds to the antibody, this indicates that the antibody is specific for phencyclidine and this will prevent the tracer from binding to the antibody. Thus, there will be fewer tracer-antibody complexes present in the sample, with the result that the total signal (amount of fluorescence read by an instrument such as the Abbott TD$_x$® Analyzer) will be less.

Serum samples were taken from the mice two weeks after each immunization and then analyzed on an Abbott Laboratories TD$_x$® Clinical Analyzer, available from Abbott Laboratories, Abbott Park, Ill., and on a Pandex Screen Machine (Baxter Healthcare Corporation, Mundelein, Ill.). After the fourth immunization and subsequent analysis of serum samples, four mice were chosen for use in the fusion of B-lymphocyte cells with myeloma cells. Each of these mice had been found to be producing antibodies specific for phencyclidine and phencyclidine metabolites based upon 50% displacement of total signal using 500 ng/mL of free phencyclidine in a competitive binding immunoassay with a tracer compound having the structure shown in FIG. 14.

Four days prior to fusing mouse B-lymphocyte cells with myeloma cells, 250 ug of the same immunogen was reinjected into one of the four responding mice in each of the two ventral peritoneal cavities (500 ug total).

B-lymphocyte cells were then removed from the mouse by standard procedures. Generally, the mouse was sacrificed, doused with 70% EtOH, and then the spleen was asceptically removed with sterile instruments. The spleen was washed in IMDM (Iscove's Modified Dulbecco's Medium) with 1% pen-strep and 1% L-glutamine and transferred to a petri dish. Using a 23 g needle on a 12 mL syringe, 20 holes were punctured into the spleen. Also using the syringe, the B-lymphocyte cells were flushed out of the spleen with two injections of 10 mL of IMDM with 1% pen-strep and 1% L-glutamine. Using a cell scraper, the spleen was gently pressed while the B-lymphocyte cells were continuously flushed out until the spleen appeared translucent. The resulting B-lymphocyte cell suspension was then filtered through Nytex filters (Tetko, Elmsford, N.Y.) into a 50 mL centrifuge tube. The B-lymphocyte cell suspension was then centrifuged for 5 minutes at 1000 rpm. After centrifugation, the supernate was aspirated off, and the B-lymphocyte cell suspension was resuspended in 10 mL of IMDM with 1% pen-strep and 1% L-glutamine. The cells were then counted using a hemocytometer to obtain the concentration of cells per mL of IMDM with 1% pen-strep and 1% L-glutamine.

Myeloma cells to be used in the production of hybridomas may be obtained from the American Type Culture Collection, Rockville, Md. They must be in a healthy log phase with viability of greater than 95%. The most desirable myelomas are those of low passage number (those obtained from a fresh stock). In addition, in a fusion of myeloma cells with B-lymphocyte cells, the number of myeloma cells should preferably be in a one to one ratio with the number of B-lymphocyte cells.

SP2/0 myeloma cells were centrifuged for 5 minutes at 1000 rpm. After the supernate was decanted from the centrifuge tube, the B-lymphocyte cells described above were fused with SP2/0 myeloma cells in a 2:1 ratio of B-lymphocyte cells to myeloma cells using the procedures described in Kohler and Milsrein, supra, with the exception that a PEG 1450 solution, MW 1300–1600 (polyethylene glycol, American Type Culture Collection, Rockville, Md.), rather than sendal virus, was employed to fuse the myeloma cells to the B-lymphocyte cells. Generally, the pellet of myeloma cells which resulted after centrifugation was resuspended with the above-described B-lymphocyte cell suspension, and then the resulting suspension was centrifuged for 5 minutes at 1000 rpm. The supernate was then aspirated from the centrifuge tube, leaving a very dry pellet. The pellet was loosened by gently tapping the bottom of the centrifuge tube on a hard object and 1 mL of a PEG 1450 solution (prepared by diluting 1 mL of PEG 1450 solution with 2 mL of IMDM with 1% pen-strep and 1% L-glutamine) was slowly added to the loosened pellet for about 10 seconds. The centrifuge tube was then rotated to ensure the even distribution of the PEG solution throughout the cell mixture for about 20 seconds. The resulting fusion mixture was then slowly resuspended with 10 mL IMDM with 1% pen-strep and 1% L-glutamine and then centrifuged for 5 minutes at 1000 rpm. The supernate was then aspirated and the resulting pellet was slowly resuspended with 10 mL of HAT selective IMDM [IMDM plus 1% 1-glutamine, 1% pen-strep, 1% HAT media (Gibco, Grand Island, N.Y.) and 10% fetal bovine serum (Hyclone, Logan, Utah)] and then plated out at a concentration of $3 \times 10^5$ cells per well in HAT selective IMDM in 96-well tissue culture plates (Nunc, Naperville, Ill.). STM mitogen (RIBI Immunochem, Hamilton, Mont.) was added to the initial plating media in order to promote hybrid survival. Hybrid colonies which resulted were fed with HT media [IMDM plus 1% 1-glutamine, 1% penn-strep, 1% HT (Gibco, Grand Island, N.Y.) and 10% fetal bovine serum (Hyclone, Logan, Utah)] on days 5 and 7 post fusion.

All resulting colonies were analyzed on day 10 with the Pandex Screen Machine described above. Those hybrids which produced antibodies in which 50% of the Total signal was displaced by 500 ng/mL free phencyclidine were cloned.

The cloning of the hybrids was performed by limiting dilution in HT media. Generally, the following dilutions of hybrids were prepared using HT media:

(a) 0.1 mL cell suspension in 9.9 mL media;
(b) 0.11 mL of (a) was added to 10.89 mL of media resulting in a $1 \times 10^{-4}$ dilution of cells;
(c) 1.1 mL of (b) was added to 9.9 mL of media, resulting in a $1 \times 10^{-5}$ dilution of cells; and
(d) 1.1 mL of (c) was added to 8.9 mL of media, resulting in a $1 \times 10^{-6}$ dilution of cells.

The $1 \times 10^{-4}$, $1 \times 10^{-5}$ and $1 \times 10^{-6}$ dilutions were then each plated out in a 96-well plate (0.1 mL/well). Each plate was fed with 0.1 mL/well HT media 5 to 7 days after cloning. The clones were screened, as described below, when confluent growth became apparent, approximately 10–14 days after cloning.

A true clone is defined as a cell originating from a cloning plate which has < or = 10% growth and passes the screening specifications described below.

Clone selection was based on the ability of the antibodies produced by the clones to: (1) displace the tracer described above with 500 ng/mL of free phencyclidine (greater than 80% displacement); and (2) not be inhibited by the initial cross reactivity panel of 10 different compounds (greater than 50% with respect to each of amitriptyline, nortriptyline, imipramine, desipramine, dextromethorphan, levallorphan, promazine, ketamine, orphenadrine, diphenhydramine, each of which was tested at 100 ug/mL in PBS).

Ascites material was generated from the clones described directly above using pristane primed female BALB/c mice. This material was then purified by Protein A—Sepharose column chromatography as described by Ey et al., "Isolation of Pure IgG1, IgG2a and IgG2b Immunoglobulins from Mouse Serum Using Protein A Sepharose," *Immunochem*, 15:429–436 (1978).

The most preferred of these hybridoma cell lines (BALB/c mouse B-lymphocyte-SP2/O myeloma fusion cell lines), or clone cell lines, was designated PCP 2-101-189, was deposited on May 16, 1990, with the American Type Culture Collection (ATCC), Rockville, Md., USA, and was given accession number HB10456 by the ATCC.

All patents and publications referred to herein are hereby incorporated by reference into this document.

While the various aspects of the present invention have been described herein with some particularity, those skilled in the art will recognize numerous modifications and variations that remain within the spirit of the invention. These modifications and variations are within the scope of the invention as described and claimed herein. The specific embodiments described herein are given by way of example only.

Various features of the present invention are set forth in the following claims.

We claim:

1. A monoclonal antibody which specifically binds phencyclidine and phencyclidine metabolites and is raised against an immunogen of the formula:

and which lacks crossreactivity with amitriptyline, nortriptyline, imipramine, desipramine, dextromethorphan, levallorphan, promazine, ketamine, orphenadrine and diphenhydramine.

2. A hybridoma which produces the monoclonal antibody of claim 1.

3. The hybridoma of claim 2 which has accession number ATCC HB 10456.

4. Hybridoma PCP 2-101-189, having accession number ATCC HB10456, or a cell line derived therefrom by passaging which expresses monoclonal antibody with the same immunological characteristics as hybridoma PCP-2-101-189.

5. A monoclonal antibody which is produced from the hybridoma cell line of claim 4 having the same immunological characteristics as the one expressed by hybridoma PCP-2-101-189.

6. A process for raising monoclonal antibodies which specifically bind phencyclidine and phenycyclidine metabolites comprising (a) immunizing animals with an immunogen of the formula:

wherein:

Q is a poly(amino acid) or poly(amino acid) derivative,

Z is NH, CO or CNH, n is zero or one when W is N and one when W is CH,

R is a linking group having a total of from 0 to 8 carbon atoms and heteroatoms, including up to 4 heteroatoms selected from the group consisting of O, N, S, P, or F with the proviso that neither S nor P is directly linked to W, and W is CH or N (b) screening the sera from the immunized animals for binding activity to phencyclidine;

(c) preparing hybridomas from B-lymphocyte cells of the animals whose sera show the binding activity to phencyclidine;

(d) selecting those hybridomas which express monoclonal antibodies which specifically bind phencyclidine and its metabolites.

7. The process of claim 6 wherein the monoclonal antibodies lack cross reactivity with amitriptyline, nortriptyline, imipramine, desipramine, dextromethorphan, levallorphan promazine, ketamine, orphenadrine and diphenhydramine.

8. A monoclonal antibody produced by the process of claim 7.

9. A process for detecting the presence or amount of phencyclidine and phencyclidine metabolites in a sample which comprises:

(a) contacting the sample with monoclonal antibodies which specifically bind phencyclidine and phencyclidine metabolites and is raised against an immunogen of the formula:

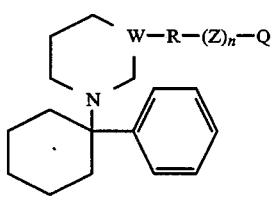

wherein;

Q is a poly(amino acid) or poly(amino acid) derivative,

Z is NH, CO or CNH, n is zero or one when W is N and one when W is CH,

R is a linking group having a total of from 0 to 8 carbon and heteroatoms, including up to 4 heteroatoms selected from the group consisting of O, N, S, P, or F with the proviso that neither S nor P is directly linked to W, and W is CH or N and which lack crossreactivity with amitriptyline, nortriptyline, imipramine, desipramine, dextromethorphan, levallorphan, promazine, ketamine, orphenadrine and diphenhydramine, and a compound of the formula:

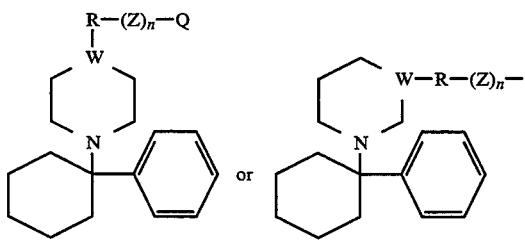

wherein:

Q is fluorescein, or a fluorescein derivative,

Z is NH, CO or CNH, n is zero or one when W is N and one when W is CH,

R is a linking group having a total of from 0 to 8 carbon atoms and heteroatoms, including up to 4 heteroatoms selected from the group consisting of O, N, S, P, or F with the proviso that neither P nor S is directly linked to W, and W is CH or N, and (b) passing plane polarized light through the resulting solution from step (a) to obtain a fluorescence polarization response; and (c) detecting the fluorescence polarization response of the solution of step (b) as a measure of the presence and amount of phencyclidine and/or phencyclidine metabolites in the sample.

10. The process of claim 9 which further comprises the step of adding a sufficient amount of dimethylformamide and a sufficient amount of butanol to wash the probe of an instrument used to conduct the process.

11. A kit for detecting the presence or amount of phencyclidine and phencyclidine metabolites in a sample which comprises:

(a) monoclonal antibodies which specifically bind phencyclidine and phencyclidine metabolites and are raised against an immunogen of the formula:

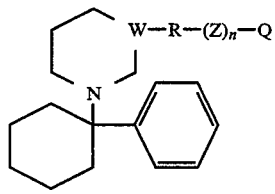

wherein:

Q is a poly(amino acid) or poly(amino acid) derivative,

Z is NH, CO or CNH, n is zero or one when W is N and one when W is CH,

R is a linking group having a total of from 0 to 8 carbon atoms and heteroatoms, including up to 4 heteroatoms selected from the group consisting of O, N, S, P, or F with the proviso that neither S nor P is directly linked to W, and W is CH or N and which lack crossreactivity with amitriptyline, nortriptyline, imipramine, desipramine, dextromethorphan, levallorphan, promazine, ketamine, orphenadrine and diphenhydramine, and (b) a compound of the formula:

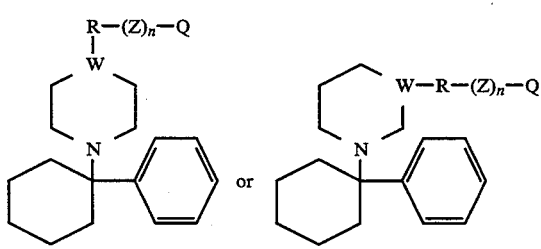

wherein:

Q is fluorescein, or a fluorescein derivative,

Z is NH, CO or CNH, n is zero or one when W is N and one when W is CH,

R is a linking group having a total of from 0 to 8 carbon atoms and heteroatoms, including up to 4 heteroatoms selected from the group consisting of O, N, S, P, or F with the proviso that neither S nor P is directly linked to W, and W is CH or N.

12. The kit of claim 11 which further comprises a sufficient amount of dimethylformamide and a sufficient amount of butanol to wash the probe of an instrument used to detect the presence or amount of phencyclidine and/or phencyclidine metabolites in a sample.

* * * * *